(12) United States Patent
Wolkin et al.

(10) Patent No.: US 7,473,031 B2
(45) Date of Patent: Jan. 6, 2009

(54) RESISTIVE THERMAL SENSING

(75) Inventors: Michal V. Wolkin, Los Altos, CA (US); Dirk De Bruyker, Palo Alto, CA (US); Eric Peeters, Fremont, CA (US); Alan Bell, Mountain View, CA (US)

(73) Assignee: Palo Alto Research Center, Incorporated, Palo Alto, CA (US)

( * ) Notice: Subject to any disclaimer, the term of this patent is extended or adjusted under 35 U.S.C. 154(b) by 149 days.

(21) Appl. No.: 11/167,748

(22) Filed: Jun. 27, 2005

(65) Prior Publication Data

US 2005/0238080 A1    Oct. 27, 2005

Related U.S. Application Data

(63) Continuation-in-part of application No. 10/114,611, filed on Apr. 1, 2002, now Pat. No. 7,141,210.

(51) Int. Cl.
*G01K 17/00* (2006.01)
*G01N 25/00* (2006.01)

(52) U.S. Cl. .................... 374/31; 374/12; 422/51

(58) Field of Classification Search .................... 374/31, 374/12; 422/51
See application file for complete search history.

(56) References Cited

U.S. PATENT DOCUMENTS

| | | | |
|---|---|---|---|
| 4,863,808 A | 9/1989 | Sallo | |
| 5,265,417 A | 11/1993 | Visser et al. | |

(Continued)

FOREIGN PATENT DOCUMENTS

| | | |
|---|---|---|
| DE | 19947788 A1 | 4/2001 |
| WO | WO 99/54730 | 10/1999 |
| WO | WO 01/85978 A2 | 11/2001 |

OTHER PUBLICATIONS

Torres, F.E., Kuhn, P., De Bruyker, D., Bell, A.G., Wolkin, M.V., Peeters, E., Williamson, J.R., Anderson, G.B., Schmitz, G.P., Recht, M.I., Schweizer, S., Scott, L.G., Ho, J.H., Elrod, S.A., Schultz, P.G., Lerner, R.A., and Bruce, R.H., "Enthalpy arrays", Proceedings of the National Academy of Sciences, vol. 101, No. 26, Jun. 29, 2004, pp. 9517-9522.

(Continued)

*Primary Examiner*—Gail Verbitsky
*Assistant Examiner*—Mirellys Jagan
(74) *Attorney, Agent, or Firm*—Leading-Edge Law Group, PLC; James T. Beran

(57) ABSTRACT

Thermal sensors for calorimetry can include vanadium oxide, heavily p-doped amorphous silicon, or other materials with high temperature coefficients of resistivity. Such thermal sensors can have low noise equivalent temperature difference (NETD). For example, a thermal sensor with NETD no greater than 100 μK over a bandwidth range of approximately 3 Hz or more can include a thermistor including vanadium oxide sputtered at room temperature under conditions that yield primarily $V_2O_5$; more specifically, the NETD can be no greater than 35 μK, or even 10 μK over a bandwidth range of approximately 3 Hz or more. If a low noise thermal sensor has NETD no greater than 50 μK over such a bandwidth range, a low noise output circuitry connected to its thermistor can provide an electrical output signal that includes information about input thermal signal peaks with amplitude of approximately 100 μK.

24 Claims, 18 Drawing Sheets

U.S. PATENT DOCUMENTS

| | | | |
|---|---|---|---|
| 5,286,976 | A | 2/1994 | Cole |
| 5,450,053 | A | 9/1995 | Word |
| 5,451,371 | A | 9/1995 | Zanini-Fisher et al. |
| 5,486,337 | A * | 1/1996 | Ohkawa ..................... 422/100 |
| 5,805,049 | A * | 9/1998 | Yamada et al. ................. 338/25 |
| 5,813,764 | A | 9/1998 | Visser et al. |
| 5,814,200 | A | 9/1998 | Pethig et al. |
| 5,850,098 | A | 12/1998 | Butler et al. |
| 5,858,306 | A | 1/1999 | Oh et al. |
| 5,924,996 | A | 7/1999 | Cho et al. |
| 5,967,659 | A | 10/1999 | Plotnikov et al. |
| RE36,615 | E * | 3/2000 | Wood .......................... 338/18 |
| 6,040,193 | A | 3/2000 | Winkler et al. |
| 6,079,873 | A | 6/2000 | Cavicchi et al. |
| 6,096,559 | A | 8/2000 | Thundat et al. |
| 6,127,914 | A * | 10/2000 | Sasaki ..................... 338/22 R |
| 6,193,413 | B1 | 2/2001 | Lieberman |
| 6,261,431 | B1 | 7/2001 | Mathies et al. |
| 6,284,113 | B1 | 9/2001 | Bjornson et al. |
| 6,294,063 | B1 | 9/2001 | Becker et al. |
| 6,319,469 | B1 | 11/2001 | Mian et al. |
| 6,331,074 | B1 | 12/2001 | Kimura |
| 6,380,605 | B1 | 4/2002 | Verhaegen |
| 6,436,346 | B1 * | 8/2002 | Doktycz et al. ............... 422/51 |
| 6,528,789 | B1 | 3/2003 | Oda |
| 6,545,334 | B2 | 4/2003 | Verhaegen |
| 6,648,503 | B2 | 11/2003 | Tanaka et al. |
| 6,649,343 | B1 * | 11/2003 | Hirota et al. ................... 435/6 |
| 6,667,479 | B2 | 12/2003 | Ray |
| 6,701,774 | B2 | 3/2004 | Srinivasan et al. |
| 6,843,596 | B2 | 1/2005 | Verhaegen |
| 6,988,826 | B2 * | 1/2006 | Zribi et al. ..................... 374/31 |
| 7,141,210 | B2 | 11/2006 | Bell et al. |
| 7,147,763 | B2 | 12/2006 | Elrod et al. |
| 2002/0003830 | A1 | 1/2002 | Tanaka et al. |
| 2002/0021740 | A1 | 2/2002 | Danley |
| 2003/0152128 | A1 | 8/2003 | Verhaegen |
| 2003/0183525 | A1 | 10/2003 | Elrod et al. |
| 2003/0186453 | A1 | 10/2003 | Bell et al. |
| 2003/0186454 | A1 | 10/2003 | Bruce et al. |
| 2003/0186455 | A1 | 10/2003 | Bruce et al. |
| 2004/0038227 | A1 | 2/2004 | Verwaerde et al. |
| 2004/0038228 | A1 | 2/2004 | Verhaegen |
| 2005/0254552 | A1 | 11/2005 | Bruce et al. |
| 2005/0254994 | A1 | 11/2005 | Bell et al. |
| 2005/0265898 | A1 | 12/2005 | Bell et al. |
| 2006/0078999 | A1 | 4/2006 | Bell et al. |
| 2006/0132542 | A1 | 6/2006 | De Bruyker et al. |
| 2006/0159585 | A1 * | 7/2006 | Torres et al. ................... 422/51 |

OTHER PUBLICATIONS

"What is a Lock-in Amplilfier?", PerkinElmer Instruments Technical Note TN 1000, 2000, pp. 1-4.

U.S. Appl. No. 11/018,757, filed Dec. 2004, pp. 1-21 and 9 sheets of drawings.

Aita, C.R., Liu, Y.-L., Kao, M.L., and Hansen, S.D., "Optical behavior of sputter-deposited vanadium pentoxide", J. Appl. Phys., vol. 60, No. 2, Jul. 15, 1986, pp. 749-753.

Razavi, A., Hughes, T., Antinovitch, J., and Hoffman, J., "Temperature effects on structure and optical properties of radio-frequency sputtered VO2", J. Vac. Sci. Technol. A, vol. 7, No. 3, May/Jun. 1989, pp. 1310-1313.

Hooge, F.N., "1/f noise is no surface effect", Physics Letters, vol. 29A, No. 3, 1969, pp. 139-140.

Johanson, R.E., Gunes, M., Kasap, S.O., "1/f Noise in doped and undoped amorphous silicon", Journal of Non-Crystalline Solids, 2000, pp. 242-246.

Khera, G.M. and Kakalios, J., "Temperature and doping dependence of non-Gaussian 1/f noise and noise statistics in hydrogenated amorphous silicon", Physical Review B, vol. 56, No. 4, Jul, 15, 1997, pp. 1918-1927.

Washizu, M., "Electrostatic Actuation of Liquid Droplets for Microreactor Applications". IEEE Transactions on Industry Applications, vol. 34, No. 4, Jul./Aug. 1998, pp. 732-737.

Pierce, M.M., Raman, C.S., Nall, B.T., "Isothermal Titration Calorimetry of Protein-Protein Interactions", Methods, vol. 19, 1999, pp. 213-221.

Johannessen, E.A., Weaver, J.M.R., Cobbold, P.H., and Cooper, J.M., "A Suspended Membrane Nanocalorimeter for Ultralow Volume Bioanalysis", IEEE Transactions on Nanobioscience, vol. 1, No. 1, Mar. 2002, pp. 29-36.

Johannessen, E.A., Weaver, J.M.R., Cobbold, P.H., and Cooper, J.M., "Heat conduction nanocalorimeter for pl-scale single cell measurements", Applied Physics Letters, vol. 80, No. 11, Mar. 18, 2002, pp. 2029-2031.

Fominaya, F., Fournier, T., Gandit, P., and Chaussy, J., "Nanocalorimeter for high resolution measurements of low temperature heat capacities of thin films and single crystals", Review of Scientific Instruments, vol. 68, No. 11, Nov. 1997, pp. 4191-4195.

Fowler, J., Moon, H. and Kim, C.-J., "Enhancement of Mixing by Droplet-Based Microfluidics", IEEE, 0-7803-7185-2/02, pp. 97-101.

Pollack, M.G., Fair, R.B., and Shenderov, A.D., "Electrowetting-based actuation of liquid droplets for microfluidic applications", Applied Physics Letters, vol. 77, No. 11, Sep. 11, 2000, pp. 1725-1726.

Jones, T.B., Gunji, M., Washizu, M., Feldman, M.J., "Dielectrophoretic liquid actuation and nanodroplet formation", Journal of Applied Physics, vol. 89, No. 2, Jan. 15, 2001, pp. 1441-1448.

Office communication in U.S. Appl. No. 11/167,746, mailed Jul. 9, 2007, 12 pages.

Amendment with Information Disclosure in U.S. Appl. No. 11/167,746, dated Apr. 17, 2007, 21 pages.

Office communication in U.S. Appl. No. 10/303,500, mailed Jul. 23, 2007, 7 pages, published in PAIR.

Amendment After Final Rejection in U.S. Appl. No. 10/303,500, submitted Sep. 21, 2007, 9 pages, published in PAIR.

Amendment With Request for Continued Examination in U.S. Appl. No. 10/303,500, submitted Oct. 22, 2007, 13 pages, published in PAIR.

Office communication in U.S. Appl. No. 10/303,500, mailed Dec. 27, 2007, 9 pages, published in PAIR.

Office communication in U.S. Appl. No. 11/167,746, mailed Dec. 28, 2007, 8 pages, published in PAIR.

Amendment with Information Disclosure in U.S. Appl. No. 10/303,500, submitted Mar. 26, 2008, 13 pages, published in PAIR.

Amendment with Information Disclosure in U.S. Appl. No. 11/167,746, submitted Mar. 21, 2008, 13 pages, published in PAIR.

Amendment After Final Rejection in U.S. Appl. No. 11/167,746, dated Sep. 7, 2007, 13 pages, published in PAIR.

Amendment with Request for Continued Examination in U.S. Appl. No. 11/167,746, submitted Oct. 3, 2007, 12 pages, published in PAIR.

Office communications in U.S. Appl. No. 10/303,500, mailed Jun. 30, 2008, 9 pages, published in PAIR.

Office communication in U.S. Appl. No. 11/167,746, mailed Jun. 27, 2008, 7 pages, published in PAIR.

Office communication in U.S. Appl. No. 11/167,746, mailed Aug. 11, 2008, 3 pages, published in PAIR.

Office communication in U.S. Appl. No. 11/149,632, electronically notified Jun. 10, 2008, 11 pages, published in PAIR.

Amendment With Information Disclosure in U.S. Appl. No. 10/303,500, submitted Sep. 30, 2008, 17 pages, published in PAIR.

Amendment in U.S. Appl. No. 11/167,746, submitted Sep. 2, 2008, 18 pages, published in PAIR.

Amendment in U.S. Appl. No. 11/149,632, submitted Sep. 25, 2008, 23 pages, published in PAIR.

* cited by examiner

FIG. 19
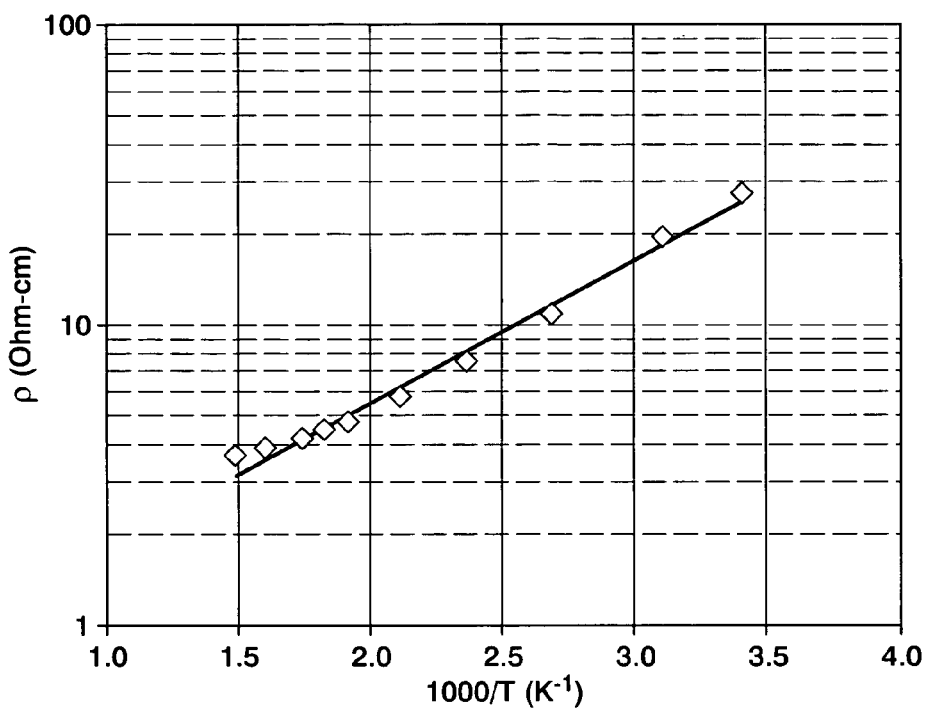
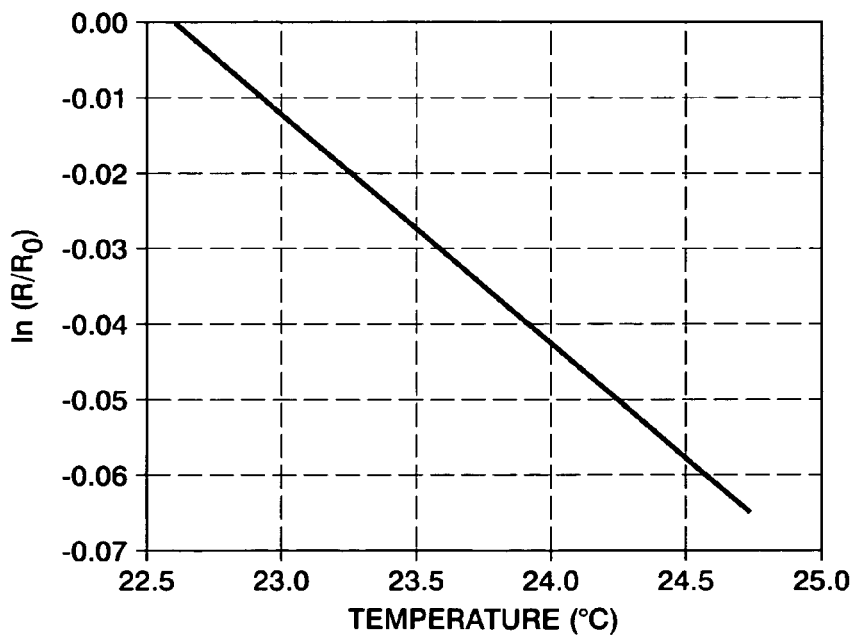
FIG. 20

| SAMPLE NUMBER | Dep T (°C) | NETD (μK) | TCR (%/K) | Rsheet (MΩ/sq) | Resistance (KΩ) | Dissipated Power (μW) |
|---|---|---|---|---|---|---|
| aSiH n+ PECVD | | | | | | |
| 1 | 230 | 68.2 | 3 | 7.5 | 315 | 3.2 |
| 2 | 275 | 68.3 | 2.8 | 5.2 | 220 | 4.5 |
| aSiH p+ PECVD | | | | | | |
| 3 | 330 | 8.3 | 3.2 | 3.8 | 160 | 6.3 |
| 4 | 330 | 10.7 | 3.1 | 4.2 | 175 | 5.7 |
| VOx Magnetron Sputtering | | | | | | |
| 5 | Room T | 6.4 | 3.1 | 0.36 | 15 | 4.0 |
| 6 | Room T | 5.9 | 3.4 | 0.89 | 37 | 4.0 |

*FIG. 21*

FIG. 22
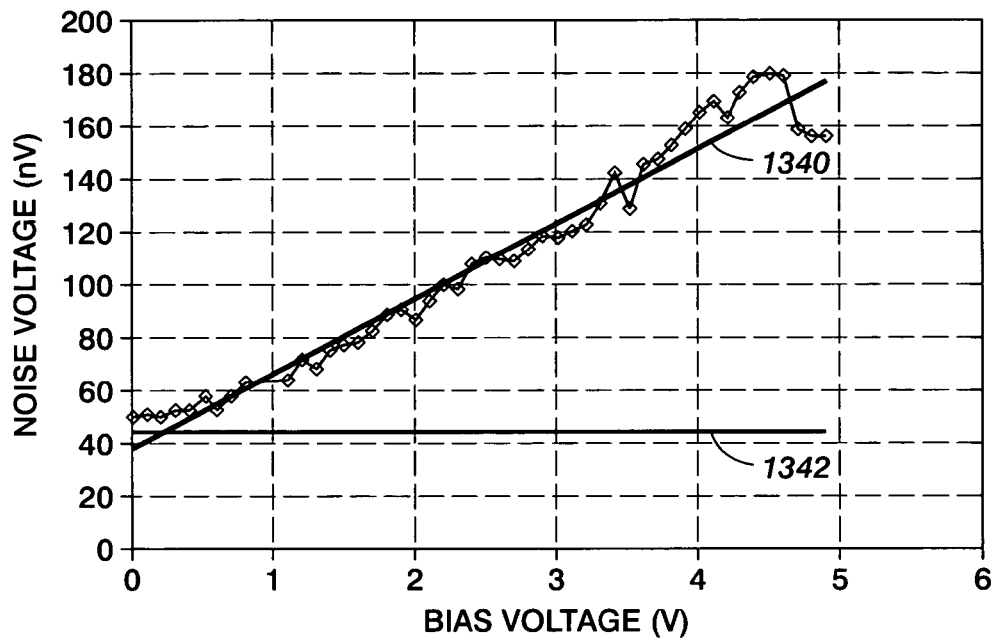
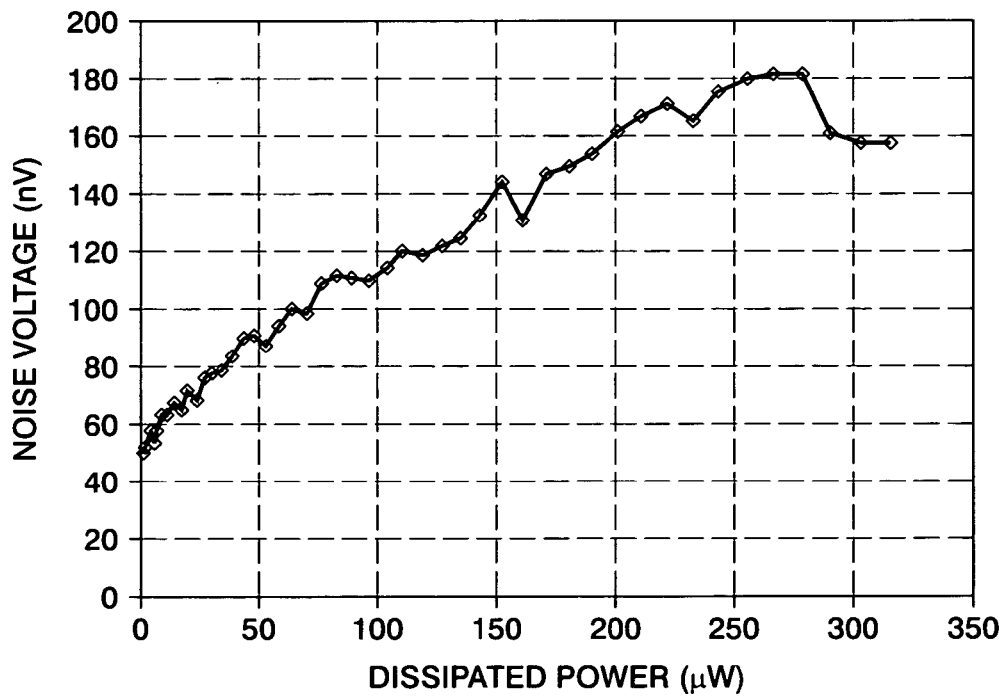
FIG. 23

FIG. 24
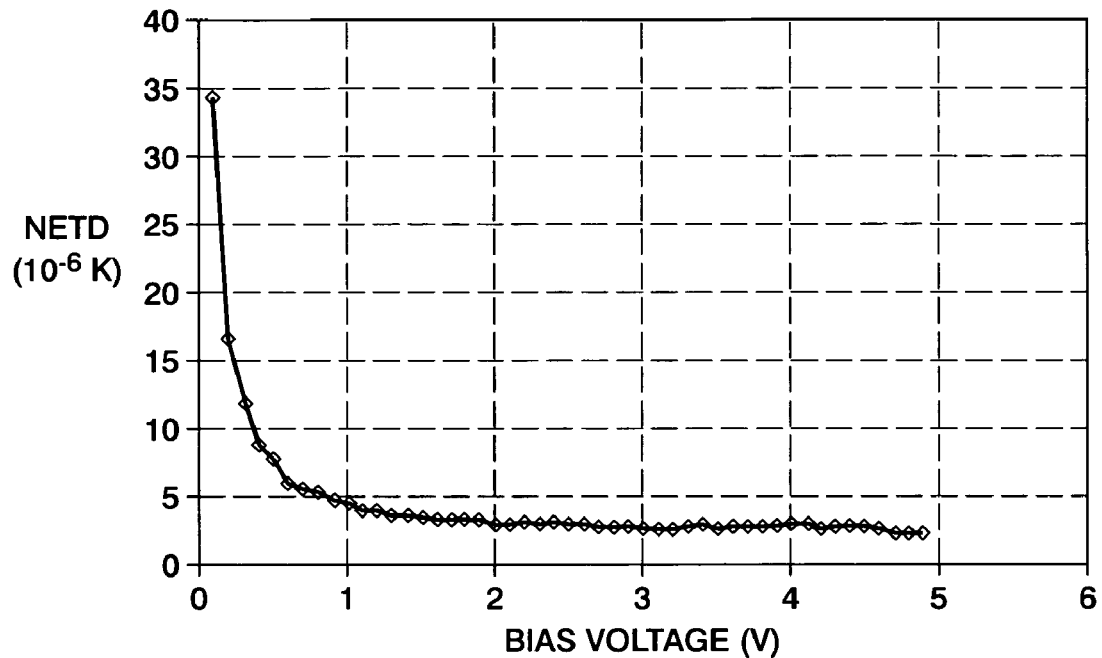
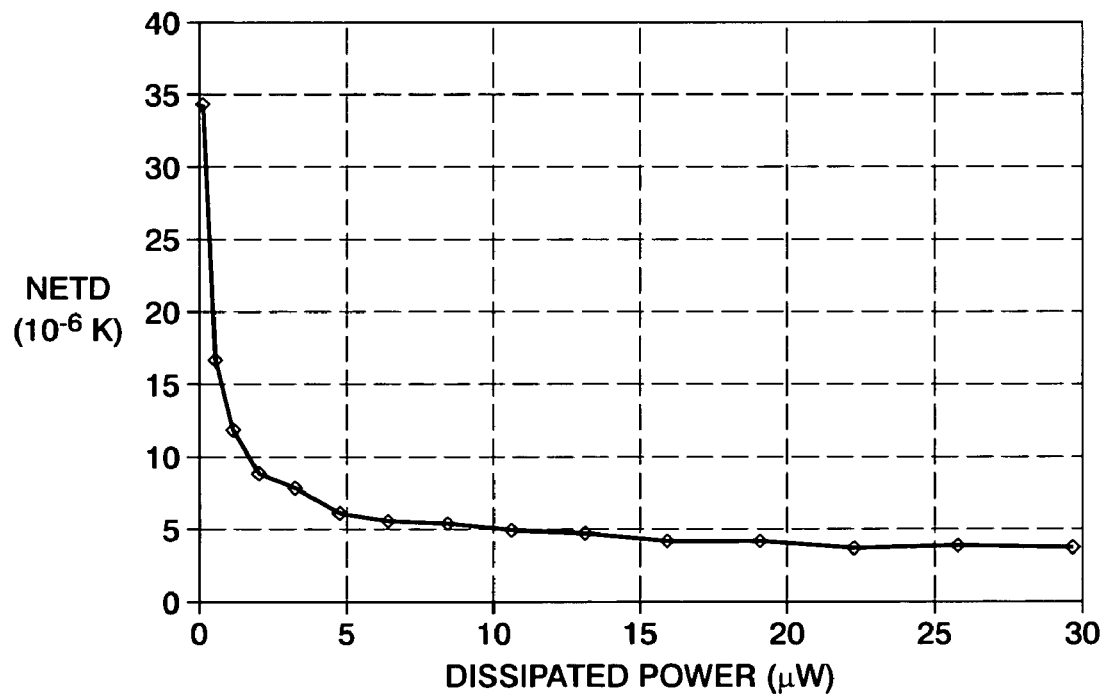
FIG. 25

RESISTIVE THERMAL SENSING

RELATED APPLICATIONS

This application is a continuation-in-part of U.S. patent application Ser. No. 10/114,611 filed Apr. 1, 2002 (U.S. Patent Application Publication No. 2003/0186453) ("the parent application") now U.S. Pat. No. 7,714,210, which is incorporated herein by reference in its entirety. Other continuations-in-part of the parent application include U.S. patent application Ser. No. 10/303,446 (U.S. Patent Application Publication No. 2003/0186454) and Ser. No. 10/303,500 (U.S. Patent Application Publication No. 2003/0186455), both of which are incorporated herein by reference in their entireties.

BACKGROUND OF THE INVENTION

The present invention relates generally to techniques that sense thermal stimuli. In particular, implementations employ thermal sensors with resistivity that varies in response to thermal stimuli. Such sensors can be used, for example, in a calorimeter, a term used herein to refer to any device or apparatus that measures quantities of absorbed or evolved heat or determines specific heats; the use of a calorimeter is referred to herein as calorimetry.

Calorimetry can measure enthalpic changes, including enthalpic changes arising from reactions, phase changes, changes in molecular conformation, temperature variations, and other variations of interest that may occur for a particular specimen. By measuring enthalpic changes over a series of conditions, other thermodynamic variables may be deduced. For example, measurements of enthalpy as a function of temperature reveal the heat capacity of a specimen, and titrations of reacting components can be used to deduce the binding constant and effective stoichiometry for a reaction.

Various resistive thermal sensors have been proposed for use in calorimetry. U.S. Pat. Nos. 3,467,501; 4,298,392; 5,312,587; and 4,021,307 describe calorimetric techniques employing thermistors. U.S. Pat. Nos. 5,265,417 and 5,451,371 describe calorimetric sensors with metallic resistors, such as platinum.

Previous techniques in sensing or detecting heat or temperature have a number of limitations. It would be advantageous to have additional techniques for resistive thermometer elements or resistive thermal sensors such as thermistors. In particular, it would be advantageous to have techniques that could be used in very sensitive calorimetry.

SUMMARY OF THE INVENTION

The invention provides various exemplary embodiments, including devices, apparatus, calorimeters, arrays, and methods. In general, each embodiment involves one or more resistive thermometer elements or resistive thermal sensors such as thermistors.

These and other features and advantages of exemplary embodiments of the invention are described below with reference to the accompanying drawings, in which like reference numerals refer to components that are alike or similar in structure or function.

BRIEF DESCRIPTION OF THE DRAWINGS

FIG. 19 is a graph of resistivity as a function of inverse temperature for a sample of vanadium oxide.

FIG. 20 is a graph of ln(R/RO) as a function of temperature in a range around room temperature, again for a sample of vanadium oxide.

FIG. 21 is a table showing noise data for materials that can be used in a thermal sensor.

FIG. 22 is a graph of noise voltage as a function of bias voltage for a sample of vanadium oxide.

FIG. 23 is a graph of noise voltage as a function of dissipated power for a sample of vanadium oxide.

FIG. 24 is a graph of noise equivalent temperature difference (NETD) as a function of bias voltage for a sample of vanadium oxide.

FIG. 25 is a graph of NETD as a function of dissipated power for a sample of vanadium oxide.

DETAILED DESCRIPTION

Figure 1:
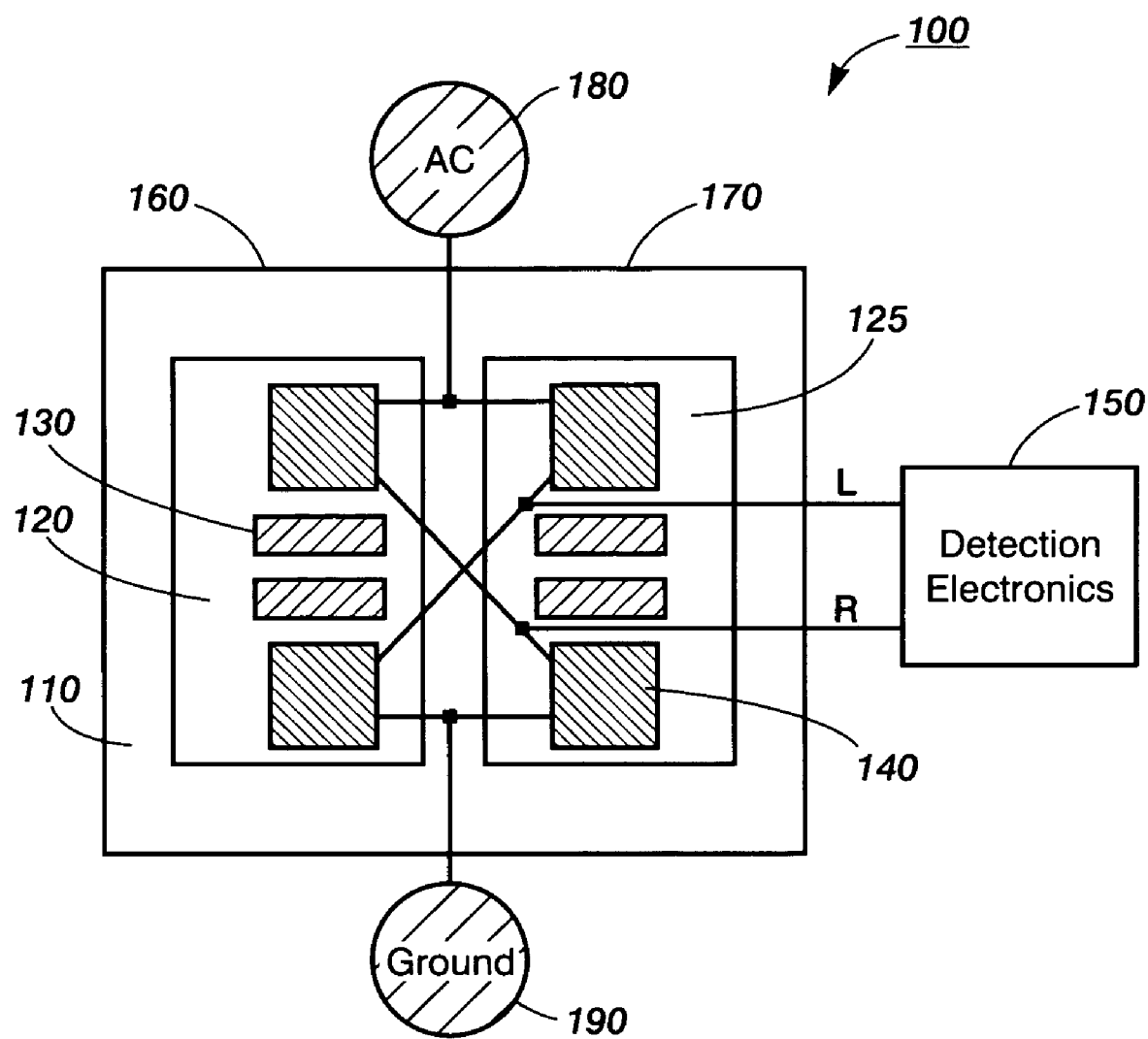
FIG. 1 is a schematic plan view depicting components of a first nanocalorimeter implementation.

The below-described implementations can be applied in measuring thermal effects of chemical reactions as well as in various other ways, some of which are described in the parent application, incorporated herein by reference. In describing some implementations, the terms "target molecule", "ligand", "test ligand", "target protein", and other terms are used herein with substantially the same meanings as set forth in the parent application.

As used herein, the term "thermal change" encompasses the release of energy in the form of heat or the absorption of energy in the form of heat.

As used herein, a "nanocalorimeter" is a calorimeter capable of measuring in the range of nanocalories. Exemplary implementations of the present invention can be applied generally in calorimeters and calorimeter arrays. More specifically, implementations can be applied in nanocalorimeters and nanocalorimeter arrays that enable measurement of enthalpic changes, such as enthalpic changes arising from reactions, phase changes, changes in molecular conformation, and the like. Furthermore, combinatorial methods and high-throughput screening methods can use such nanocalorimeters in the study, discovery, and development of new compounds, materials, chemistries, and chemical processes, as well as high-throughput monitoring of compounds or materials, or high-throughput monitoring of the processes used to synthesize or modify compounds or materials.

Compounds or materials can be identified by the above methods and their therapeutic uses (for diagnostic, preventive or treatment purposes), uses in purification and separation methods, and uses related to their novel physical or chemical properties can then be determined. The parent application, incorporated herein by reference, describes use of high-throughput screening methods and other such techniques in various applications.

Various techniques have been developed for producing structures with one or more dimensions smaller than 1 mm. In particular, some techniques for producing such structures are referred to as "microfabrication." Examples of microfabrication include various techniques for depositing materials such as growth of epitaxial material, sputter deposition, evaporation techniques, plating techniques, spin coating, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In general, the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes. Also, a support structure could be a "support layer", meaning a layer of material that can support other structures; for example, a support layer could include a polymer film and a barrier layer on a side of the polymer film.

A structure or component is "directly on" a surface when it is both over and in contact with the surface. A structure is "fabricated on" a surface when the structure was produced on or over the surface by microfabrication or similar processes. A process that produces a layer or other accumulation of material over or directly on a substrate's surface can be said to "deposit" the material.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

FIG. 1 shows a plan view of nanocalorimeter detector 100, a first implementation of a detector that can be used in a nanocalorimeter array. This implementation enables a passive thermal equilibration of the combined protein, water, and ligand drops with the device so that the resultant temperature changes can be detected by means of a temperature-sensing device. Suitable thermometer elements are based on thin film materials and include various resistive thermometer elements, resistive thermal sensors, thermistors, and so forth, examples of which are described below.

Because the measurement region is kept small enough and sufficiently thermally conductive, through the use of a thermally conducting layer such as aluminum or copper, the passive equilibration time will be small. As used herein, the terms "thermally conducting" or "thermally conductive" are applicable to any component, layer, or other structure that sufficiently conducts thermal signals from one position or region to another that the thermal signals can affect concurrent thermally sensitive operations in the other position or region. For example, if the thermal signals include information, the information could be available for sensing and electrical detection in the other position or region. Two components are in "thermal contact" even if not in direct contact if a structure between them is conductive for thermal signals of interest. More generally, thermal signals may follow a "thermally conductive path" between two components, meaning a path along which the signals are conducted.

The term "sensing" is used herein in the most generic sense of obtaining information from a physical stimulus; sensing therefore includes actions such as detecting, measuring, and so forth. A "thermal sensor" is accordingly used herein to refer to an element or combination of elements that senses at least one thermal stimulus such as heat, temperature, or random kinetic energy of molecules, atoms, or smaller components of matter. A "resistive thermal sensor" is a thermal sensor with electrical resistance that varies with the thermal stimulus that it senses, in contrast to various thermal sensors that sense in other ways such as with thermocouples or thermopiles. The terms "resistive thermometer element" and "resistive thermometer" similarly refer to an element of any kind with electrical resistance that varies with temperature. As used herein, the term "thermistor" means an electrically resistive component that includes semiconductor material with resistance that varies in response to a thermal change; a thermistor can therefore be employed in a resistive thermal sensor or a resistive thermometer. In each of these definitions, variation in resistance would include both linear and non-linear variations; a non-linear variation might occur in a thermistor, for example, if a temperature change causes a phase change in the semiconductor material.

Resistive thermal sensors and resistive thermometers can, for example, be made from materials with a high temperature coefficient of resistivity (TCR) in comparison with those of other materials. Examples of semiconductor materials with high TCR include amorphous silicon, vanadium oxide ($VO_x$), yttrium barium copper oxide (YBCO), and mercury cadmium telluride. Other materials that have been used in resistive thermal sensors include, for example, platinum, nickel, copper, iron-nickel alloys such as balco, tungsten, iridium, oxides of nickel, manganese, iron, cobalt, copper, magnesium, and titanium, and other metals, metal alloys, and oxides of metal. Any, such material is referred to herein as a "high TCR material". Furthermore, unless otherwise specified, the terms "vanadium oxide" and "$VO_x$" refer herein to any oxide or combination of oxides of vanadium that can be used in the context, such as $V_2O_5$, $VO_2$, $V_2O_3$, VO, and so forth.

Nanocalorimeter detector 100 includes thermal isolation layer 110, which contains measurement region 160 and reference region 170. Regions 160 and 170 may also be contained in separate isolation regions, as described hereinbelow. Thermal isolation layer 110 provides isolation from surrounding thermal environments, thus increasing measurement time and reducing thermal noise, also referred to herein as Johnson noise, i.e. the theoretical minimum achievable noise level. Although layer 110 is used in this implementation to thermally isolate the reaction and temperature sensing components of the nanocalorimeter detector 100, any means to thermally isolate these components can be used in alternate implementations.

As used herein, the terms "thermal isolation" or "thermal isolating" are applicable to any layer or other structure that sufficiently prevents conduction of or fails to conduct thermal signals from one region to another, so that the thermal signals do not affect concurrent thermally sensitive operations in the other region. A thin layer, for example, may be thermally isolating in its lateral directions, i.e. directions approximately parallel to its surfaces, but may permit thermal conduction in its thickness direction, i.e. the direction perpendicular to its surfaces.

In this implementation, thermal isolation layer 110 may include a plastic material in thin foil form (typically ranging from less than 15 µm to approximately 25 µm in thickness, possibly as thin as 2 µm and as thick as 500 µm for some applications). Candidate plastic materials include polymers such as polyimide (for example DuPont Kapton® and others), polyester (for example DuPont Mylar®, DuPont Teonex® PEN, or DuPont Teijin® Tetoron® PET) foil, PolyEtherEtherKetone (PEEK), or PolyPhenylene Sulphide (PPS). Alternatively, thermal isolation layer 110 includes other thin layers of sufficiently low thermal conductivity, such as SiN and comparable materials.

Measurement region 160 and reference region 170 include thermal equilibrium regions 120 and 125 respectively, that are thermally isolated from the detector's mechanical support. In this implementation, thermal equilibrium region 120 contains two resistive thermometers 140, which measure the reaction temperature, while thermal equilibrium region 125 contains a second set of two resistive thermometers 140, which measure the variations in the background temperature. Resistive thermometers 140 can therefore be produced in thermal equilibrium regions 120 and 125 using microfabrication or other techniques, such as printed circuit board fabrication techniques.

As used herein, the term "reaction region" refers to a region in which a reaction can occur, producing thermal change. A "reaction surface" is a part of a surface that is a reaction region. Both thermal equilibrium regions 120 and 125 are reaction regions and, more specifically, reaction surfaces because they are sufficiently large to receive and support separate drops of protein and ligand deposited by direct printing and also to support the combination of these two drops after merging, triggered by an example drop merging device 130. For example, for a 400 nl final drop size, the detector, which includes the measurement and reference regions, may be 3.7 mm by 4.6 mm. Each thermal equilibrium region 120 and 125 has sufficient thermal conduction for the region to equilibrate quickly relative to thermal dissipation. The regions each have a sufficiently low heat capacity such that little of the heat of reaction is absorbed in the support. High thermal conductivity with low heat capacity may be accomplished, for example, with a metal film such as a 10 µm thick aluminum or copper film extending over the area of the thermal equilibrium region. In this example, for a 400 nl drop and a 10 µm thick aluminum film, the film absorbs approximately 7% of the heat of reaction. In general, the term "high thermal conductivity" refers herein to a thermal conductivity that is approximately as great or greater than those of aluminum and copper.

As suggested above, in this implementation the thermal equilibrium regions 120 and 125 must be thermally isolated from their environment so that the temperature difference caused by the reaction takes a relatively long time to dissipate. The longer this dissipation time, the longer the signal can be integrated during measurement, which improves the signal to noise ratio. For example, a 10 second integration time corresponds to a 0.1 Hz measurement bandwidth and increases the signal to noise ratio by 3.2 over a 1 second integration. Thermal dissipation can occur through at least four different channels: conduction across the supporting medium, conduction through the electrical interconnect, conduction through the surrounding environment and evaporation. For the example of conduction across the thermal isolation layer 110, the rate of heat transfer from the drop equals the thermal conductivity of the layer 110 multiplied by the cross section of the layer 110 through which the heat is conducted and the temperature gradient across the region, or $$Q = \Lambda A dT/dx,$$

where $\Lambda$ is the thermal conductivity of thermal isolation layer 110, A is the cross section of the region through which the heat is conducted and dT/dx is the temperature gradient across thermal isolation layer 110. Note Q=C dT/dt where C is the heat capacity of the drop, and from this $$T = T_o e^{-\Lambda A t/CL},$$

where t is the time, L is the length of the isolation layer 110, and all temperatures are relative to the temperature of the surrounding environment, with the approximation dT/dx=T/L. The time constant, $\tau$, for thermal dissipation is therefore $$\tau = CL/\Lambda A.$$

Consequently, the time constant increases with increases in the heat capacity of the drop and decreases with increases in the rate of thermal conduction. Note that while the heat capacity of the drop increases with drop size, increasing the drop size reduces the density of detectors on an array of detectors, increases the thermal equilibration time for the drop, and uses valuable material. A lower array density means a larger array size for a given detector number.

In the example implementation, drop size is 400 nl for the combined drop after merging. For this drop size, estimates of the time constants associated with different dissipation channels in one implementation are shown in the following Table 1:

TABLE 1

| Conduction Channel | Time Constant |
| --- | --- |
| Conduction across support layer + interconnect leads | 110 sec |
| Conduction through vapor (air) | 6 sec |
| Evaporation (25° C. operation) | 8 sec |

For the purposes of Table 1, it was assumed that the thermal isolation layer is 7 µm thick plastic and there are eleven interconnect leads with thickness of 0.1 µm for each thermal equilibrium region. As mentioned above, the thermal isolation layer for this example implementation may be fabricated of a plastic material in thin foil form (typically ranging from less than 15 μm to approximately 25 μm in thickness for this implementation, possibly as thin as 2 μm and as thick as 500 μm for some applications), thereby ensuring that the above time constant for conduction across the thermal isolation layer is large compared with the measurement bandwidth. Examples of candidate plastic materials include polyimide (for example Dupont Kapton®. and others), polyester (for example Dupont Mylar®, DuPont Teonex® PEN, or DuPont Teijin® Tetoron® PET) foil, PolyEtherEtherKetone (PEEK), PolyPhenylene Sulphide (PPS), polyethylene, or polypropylene. Rather than air, the vapor could be any appropriate gas or combination of gasses, such as argon or possibly xenon.

In the implementation of FIG. 1, the same material may be used for the support and the thermal equilibration, including the resistive thermometers. Consequently, one important consideration in selecting a substrate polymer is the highest temperature that is needed in subsequent deposition and processing of thermometer, conductor and insulator films in the particular implementation. As an example, the temperature needed in the deposition of amorphous silicon thermometer material is typically in the range of 170-250° C. This requires the selection of a substrate polymer film with a high softening temperature. These polymers may include, but are not limited to, polyimide, PolyEtherEtherKetone (PEEK), or PolyPhenylene Sulphide (PPS). Conversely, deposition of vanadium oxide thermometer material can be done at a substantially lower temperature such as room temperature. This allows the selection of substrate polymers with a lower softening point, such as polyester (Dupont Mylar® or DuPont Teonex® PEN).

These plastic substrates enable low cost manufacturing that can scale to large arrays of detectors, which enable fast and cost effective testing of large numbers of reactions. Detectors as in FIG. 1 could be used, for example, in detector array sizes of 96, 384, 1536 and larger. The low-cost detector arrays might also be used once and then discarded, eliminating time-consuming washing steps and reducing problems with cross-contamination.

Another thermal consideration is the characteristic time for a drop to equilibrate with the detector after it is placed on the detector. This is a combination of the characteristic time for conduction of heat through the drop, $t_1$, and the characteristic conduction time across the detector, $t_2$. In an implementation, an aluminum film is used to increase the thermal conduction across the detector. An estimate of the characteristic time $t_1$ is $$t_1 = 0.44 R^2/\alpha \approx 0.6 \text{ sec},$$

where R is the drop radius, in this example 460 μm, and a is the thermal diffusivity of the drop, 0.0015 cm$^2$/sec for water. For thin plastic substrates, the characteristic time for lateral conduction across the detector is governed by conduction across the metal film incorporated into the design for temperature equilibration, which is an aluminum strip in this example. An estimate for this characteristic time is $$t_2 = (\rho C_p V)_{drop} \times L_{Al}/4R_{drop} \times \delta \times k_{Al} \approx 0.4 \text{ sec},$$

where ρ is the density of the drop, 1 g/cm$^3$ in this example; $C_p$ is the specific heat, 1 cal/gK in this example; $L_{Al}$, is the length of the conduction path along the aluminum strip from one drop to the other, 2.5 $R_{drop}$ in this example; δ is the aluminum strip thickness, 10 μm in this example; and $k_{Al}$ is the aluminum thermal conductivity, 0.57 cal/K-cm-sec. The aluminum thickness is selected to provide sufficient thermal conduction without contributing significantly to the heat capacity of the detector. Heat capacity of the detector must be made sufficiently low so as to minimize the absorption of heat released from the reaction in the drop in order to minimize attenuation of the temperature change arising from the reaction.

Each thermal equilibrium region 120 and 125 contains thermometers 140 and drop merging electrodes 130. Although for the purposes herein thermometers 140 are shown spaced apart from more centrally-positioned drop merging electrodes 130 on each thermal equilibrium region 120 and 125, this configuration is for means of example only. Provided that the drop merging device 130 and thermometers 140 are in good thermal contact with the high conductance film, the exact placement of thermometers 140 and drop merging electrodes 130 is not important for thermal considerations.

In operation, the two resistive thermometers 140 situated in thermal equilibrium region 120 detect the heat of reaction between an arbitrary protein and a ligand at low concentrations deposited within thermal equilibrium region 120. In this example, the heat of reaction is detected through measurement of a voltage change in a bridge circuit due to the resistance change in the thermometers that are configured in the bridge circuit. This is an example of connecting or interconnecting circuitry that allows "electrical detection" of an event or characteristic, such as detection of temperature or thermal signals or of a difference between two voltages, resistances, or temperatures, meaning that the circuitry provides or can be connected to circuitry that provides an electrical signal indicating the detected event or characteristic. Within any circuitry, electrically conductive components that serve primarily to connect other components are referred to herein as "leads" or "lines."

As used herein, the term "bridge" refers to any electrical instrument or network for measuring or comparing resistances, inductances, capacitances, or impedances by comparing two voltages to each other or by comparing their ratio to a known ratio. Further, the terms "bridge circuit" and "bridge circuitry" refer to circuits and circuitry that connect or interconnect resistive elements or other elements so that they can be used in a bridge. Bridge circuitry is "capable of being driven to allow electrical detection" of a characteristic, such as detection of a difference between two voltages, resistances, or temperatures, if the bridge circuitry is or can be connected to receive drive signals and also is or can be connected to circuitry that provides an electrical signal indicating the detected characteristic when the bridge circuitry is receiving the drive signals.

Resistive thermometers 140 in thermal equilibrium region 120 detect a reaction between a sample ligand and a protein; the other resistive thermometers 140 in thermal equilibrium region 125 serve as a reference. Because the temperature rise due to the reaction may be small, for example approximately 10 μK for protein and ligand concentrations of 1 μM and a heat of reaction of 10$^4$ cal/mole, the resistive thermometers 140 are fabricated from materials that provide a large change in resistance for a small temperature change.

In this implementation, the resistive thermometers 140 are fabricated from high TCR material. Similar small drops of non-reactive solution (for example water or mixtures of water and DMSO) and target protein, the control combination, are deposited close together in thermal equilibrium region 125. Resistive thermometers 140 are configured as an AC bridge represented by AC generator 180 and ground 190, discussed in more detail hereinbelow. At a specified time after the drops have reached thermal equilibrium, they are moved together to initiate the reaction. The movement operation creates sufficient mixing of the two drops in a time small compared to the measurement time. The heat released by the protein-ligand reaction of the test combination causes a change in the resistance of the affected thermometers relative to the reference thermometers. This change in resistance causes the voltage at the detection point to change from zero. This change is detected by sensitive, noise rejecting circuits such as a lock-in amplifier within detection electronics 150.

Figure 2:
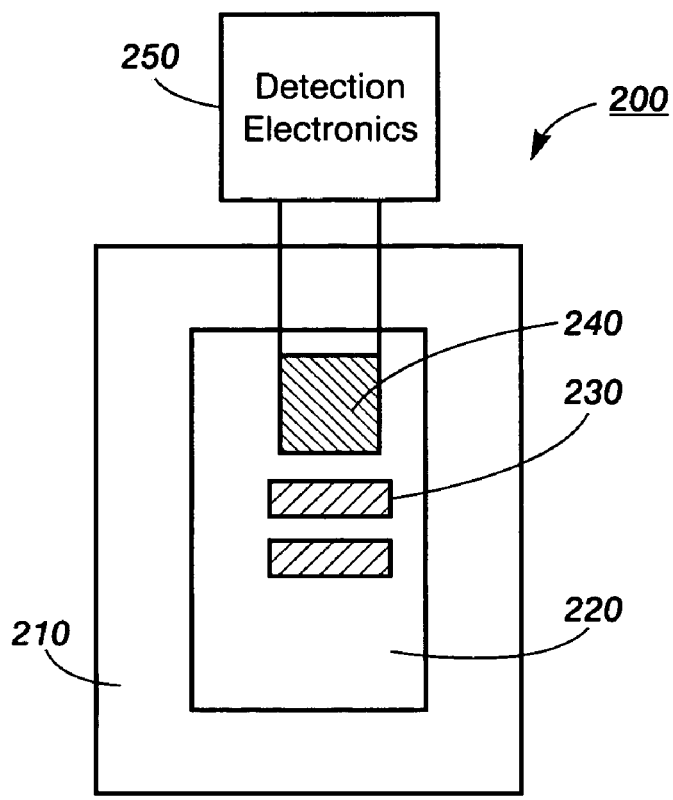
FIG. 2 is a schematic plan view depicting components of a second nanocalorimeter implementation.
Figure 3:
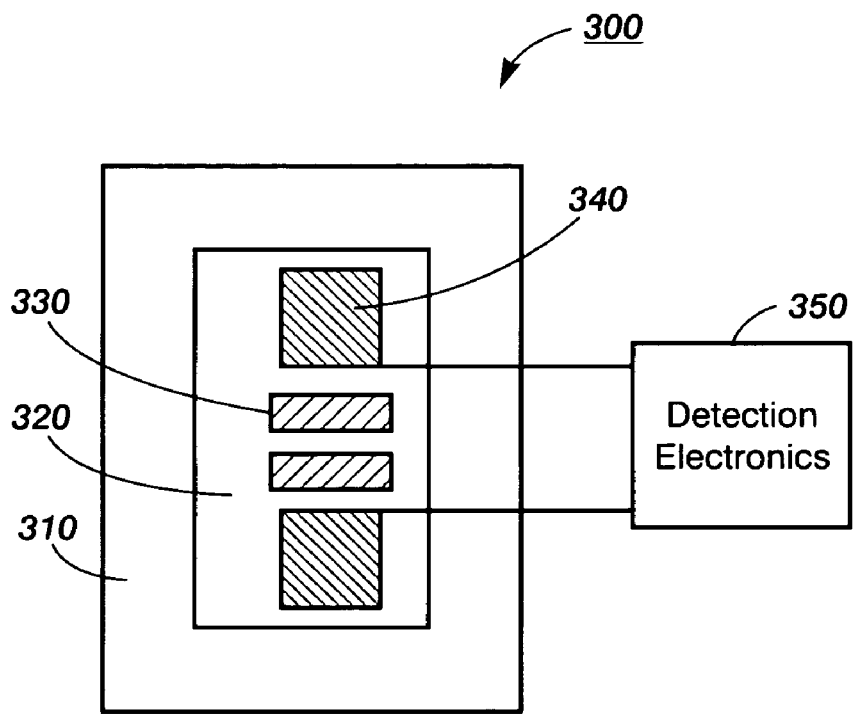
FIG. 3 is a schematic plan view depicting components of a third nanocalorimeter implementation.
Figure 4:
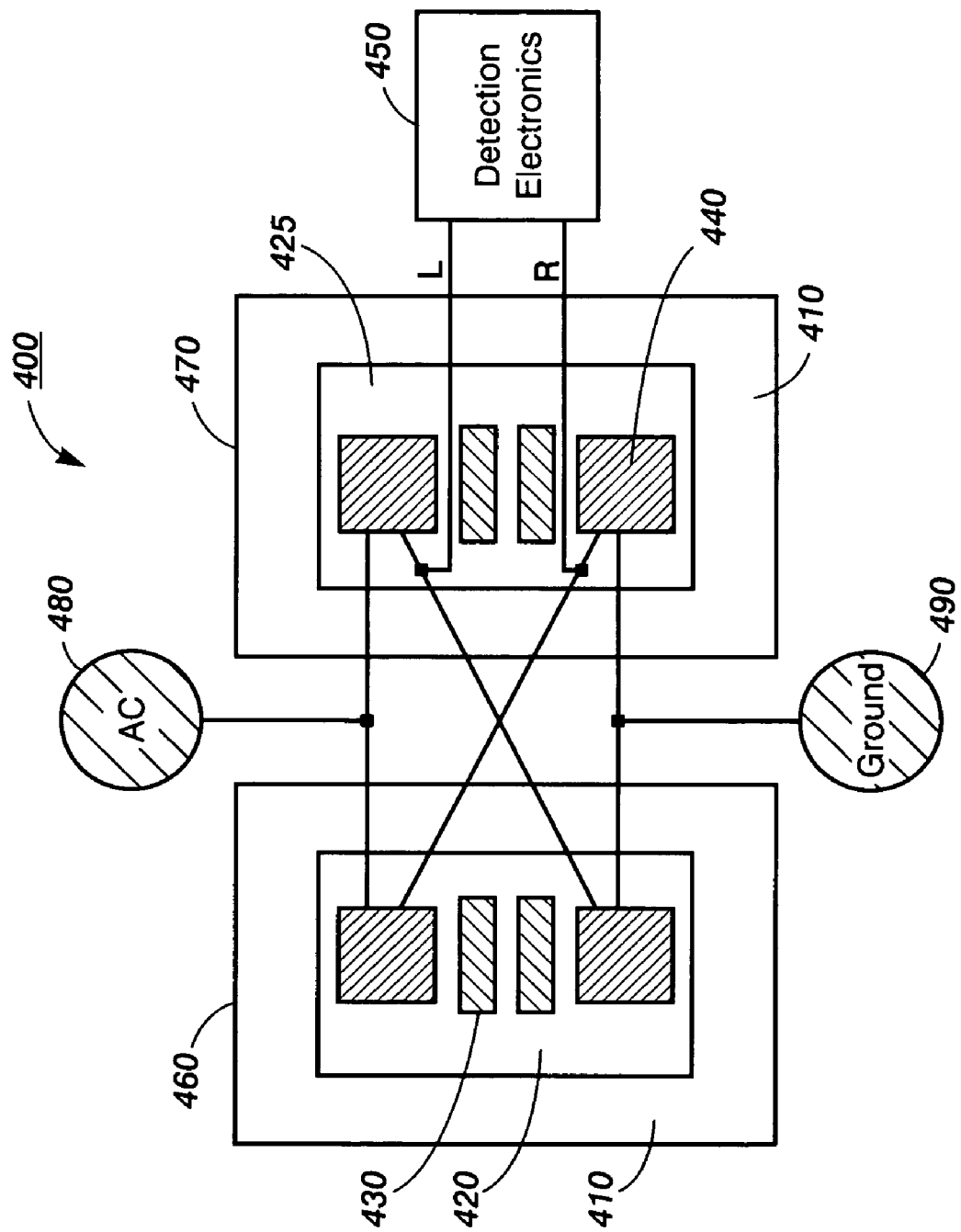
FIG. 4 is a schematic plan view depicting components of a fourth nanocalorimeter implementation.

FIGS. 2-4 show other implementations in which nanocalorimeter detectors 200, 300, and 400 include thermal isolation layers 210, 310, and 410, respectively, which contain thermal equilibrium regions 220, 320, 420, and 425. Thermal isolation layers 210, 310, and 410 provide isolation from surrounding thermal environments, thus increasing measurement time and reducing thermal noise.

In FIG. 2, thermal equilibrium region 220 contains one resistive thermometer 240, which measures the reaction temperature. In FIG. 3, thermal equilibrium region 320 contains two resistive thermometers 340, which measure the reaction temperature. In FIG. 4, thermal equilibrium regions 420 and 425 each contain two resistive thermometers 440, which measure the reaction temperature. Each resistive thermometer is produced in thermal equilibrium region 220, 320, 420, or 425 using microfabrication or other techniques, such as printed circuit board fabrication techniques.

Thermal equilibrium regions 220, 320, 420, and 425 are each sufficiently large to receive and support separate drops of protein and ligand deposited by direct printing and also to support the combination of these two drops after merging, triggered by drop merging device 230, 330, or 430. Thermal equilibrium regions 220, 320, 420, and 425 each have a sufficient thermal conduction for the region to equilibrate quickly relative to the thermal dissipation. Each region also has a sufficiently low heat capacity such that little of the heat of reaction is absorbed in the support. High thermal conductivity with low heat capacity may be accomplished, for example, with a metal film such as a 10 μm thick aluminum or copper film.

In addition to resistive thermometers, thermal equilibrium regions 220, 320, 420, and 425 contain drop merging devices 230, 330, and 430, respectively. Although thermometers 240, 340, and 440 are shown spaced apart from more centrally-positioned drop merging devices 230, 330, and 430 on thermal equilibrium regions 220, 320, 420, and 425, this configuration is for example only. Provided that the drop merging device 230, 330, or 430 and thermometer 240, 340, or 440 are in good thermal contact with the high conductance film, the exact placement of thermometer 240, 340, or 440 and drop merging device 230, 330, or 430 is not important for thermal considerations.

In operation, resistive thermometers 240, 340, and 440 situated in thermal equilibrium regions 220, 320, 420, and 425 detect the heat of reaction between reactants such as an arbitrary protein and a ligand at low concentrations deposited within thermal equilibrium regions 220, 320, 420, and 425, respectively. For example, resistive thermometers 440 situated in thermal equilibrium region 420 detect the temperature of drops deposited and merged within thermal equilibrium region 420. Similar small drops of non-reactive solution (for example water or mixtures of water and DMSO) and target protein, the control combination, are deposited close together in thermal equilibrium region 425. In this example, the heat of reaction is detected through measurement of a voltage change in a bridge circuit due to the resistance change in the thermometers, which are configured in the bridge circuit.

In general, resistive thermometers 240, 340, and 440 in thermal equilibrium regions 220, 320, and 420 detect a reaction between a sample ligand and a protein or between other suitable reactants, while resistive thermometers 440 in region 425 detect a reference reaction, such as between non-reacting fluids. Because the temperature rise due to the reaction may be small (approximately 1 mK for the implementation of FIG. 2 or, in other implementations, approximately 10 μK for protein and ligand concentrations of 1 μM and a heat of reaction of $10^4$ cal/mole), resistive thermometers 240, 340, and 440 are fabricated from material that provides a large change in resistance for a small temperature change. In these implementations, resistive thermometers 240, 340, and 440 are made of high TCR material.

Resistive thermometers 240 and 340 are each configured as one leg of an AC bridge, the other legs of which (i.e. any legs without resistive thermometers) are included in detection electronics 250. Other legs of the bridge are made, for example, of low temperature coefficient resistors located on an amplifier printed circuit board (PCB). Similarly, resistive thermometers 440 are configured as legs of an AC-biased Wheatstone bridge, driven between AC generator 480 and ground 490, discussed in more detail hereinbelow.

At a specified time after the drops have reached thermal equilibrium, they are moved together to initiate the reaction. The movement operation creates sufficient mixing of two drops in a time small compared to the measurement time. The heat released by the protein-ligand reaction of a test combination causes a change in the resistance of affected thermometers. This change in resistance causes voltage at a detection point to change from zero. This change is detected by sensitive, noise rejecting circuitry such as a lock-in amplifier. Alternatively, if the reactions to be measured produce enough heat, the resistance change of one or more thermometers could be measured by a direct DC resistance measurement, such as through two thermometers connected in series.

If implemented with vanadium oxide, each of FIGS. 1-4 thus illustrates an example of a calorimeter in which a resistive thermometer element includes vanadium oxide. The calorimeter also includes circuitry through which electrical resistance of the thermometer element can be detected, exemplified by the bridge circuits or detection electronics. The calorimeter also includes a structure with a reaction region in which reactions that produce thermal change occur, exemplified by the region in which drops are merged. The structure conducts temperature from reactions in the reaction region to the thermometer element.

Figure 5:
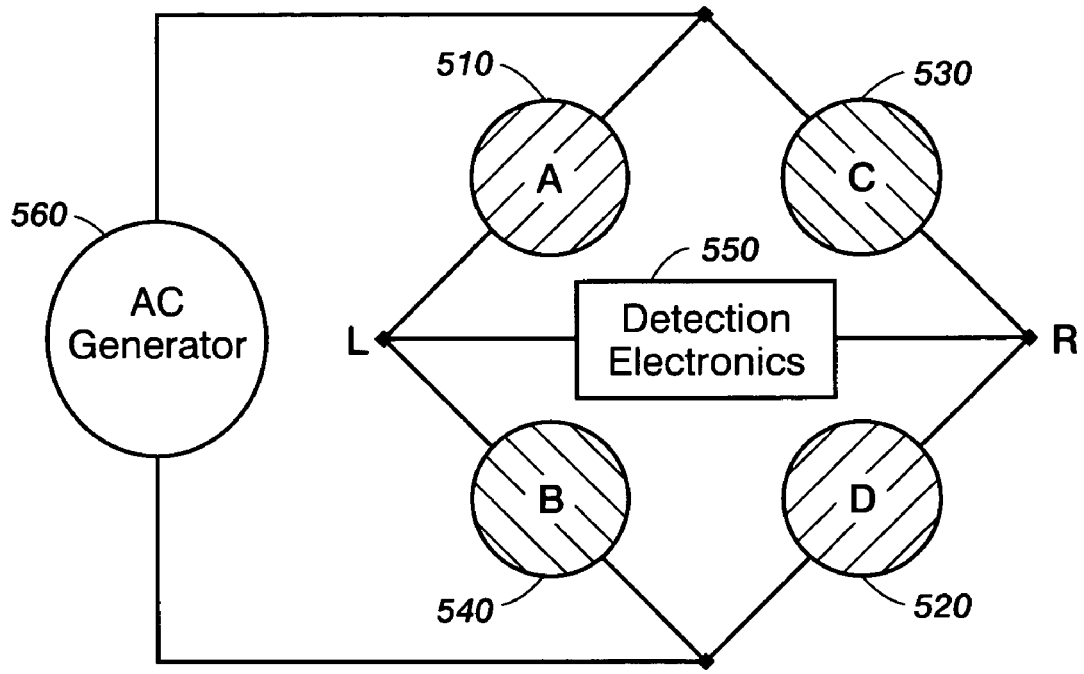
FIG. 5 is a schematic circuit diagram of a first electronic measuring system with resistive thermometer elements.

FIG. 5 shows thermometers 510, 520, 530 and 540 forming four resistive legs of one example configuration for a bridge circuit. Resistive thermometers simultaneously measure temperature changes due to both the reaction and the background drift. In this example, two measurement thermometers 530 and 540 measure the reaction and two reference thermometers 510 and 520 measure the background temperature changes. If the resistance of the measurement thermometers changes, as happens when the temperature in the measurement region increases, then the voltage at output detection point R in the bridge becomes more positive or negative relative to ground, depending on the polarity of the voltage placed across the bridge circuit and the sign of the TCR, while the voltage at output detection point L in the bridge does the opposite, that is, becomes less positive or negative relative to ground, respectively. This configuration maximizes the voltage difference across detection electronics 550. As will be appreciated by one skilled in the art, other bridge configurations are possible, such as one in which thermometer 540 has a low temperature sensitivity and is not fabricated on the device or where thermometer 520 is replaced by a variable resistor used to balance the bridge and is also not fabricated on the device.

Resistance thermometers 510, 520, 530 and 540 may be fabricated from patterned thin film and are connected as a bridge. The resistance of each thermometer varies with temperature by an amount proportional to the TCR of the material used. Since $$\alpha = 1/R(\Delta R/\Delta T),$$

it follows that $$\Delta R = \alpha R \Delta T,$$

where R is resistance, T is temperature, and $\alpha$ is the TCR of the thermometer material. Therefore, the signal voltage across the resistor varies by $$\Delta V_S = \Delta RI = \alpha R \Delta T \sqrt{\frac{P}{R}},$$

where $V_S$ is the signal voltage, I is the current through the resistor, and P is power. The thermal noise in each resistor becomes $$V_N = \sqrt{4kTRB} = 1.2 \times 10^{-10} \sqrt{RB}$$

where B is the measurement bandwidth in seconds, R is the resistance in Ohms, and k is Boltzmann's constant. Assuming the detection system can be constructed without introducing noise in excess of the thermal noise, the signal to noise ratio becomes $$S/N \approx 8.3 \times 10^9 \alpha \Delta T \sqrt{P/B}.$$

Protein-ligand reactions are generally investigated at low concentrations during high-throughput screening, typically in the range of $10^{-5}$ to $10^{-6}$ M. The reactions typically release a heat of reaction, Q, which is on the order of $10^4$ cal/mole. For illustrative purposes, consider combining two drops with concentrations of 2 μM of protein and ligand, respectively. If the drops have equal volumes, the combination has a 1 μM concentration of each reactant. Additionally, $$CV\Delta T = MVQ,$$

where V is the solution volume, C is the heat capacity of the solution, and M is the concentration in the mixed drop. Therefore, $$\Delta T = MQ/C = 10^{-6} \text{mole}/L \times 10^4 \text{cal/mole}/10^3 \text{cal}/K - L = 10^{-5} K,$$

where Q is the heat of reaction, C is the heat capacity of the solute, and M is the concentration in the mixed drop.

For example, for a thin film thermometer made from a-Si, for which $\alpha = 2.8 \times 10^{-2}$ K$^{-1}$, and a bandwidth of 0.1 Hz, a signal to noise ratio of 7 is achieved with 1 μW of power dissipated in the resistor. The voltage change then becomes $$\Delta V_S = 2\Delta RI = 2\alpha \Delta TRI = 4 \times 10^{-7} RI \approx 4 \times 10^{-7} \sqrt{PR}.$$

Table 2 of the parent application, incorporated herein by reference, provides the signal strength for various exemplary combinations of thermometer impedance and power. In current implementations, thermometer impedances are approximately 8 kΩ.

To initiate a reaction, the deposited drops need to be merged together and the drop contents well mixed. It is noted that numerous methods for drop deposition are known in the art, any of which may operate beneficially for the purpose of dispersing drops.

Although numerous means and methods for merging the deposited drops may be utilized, for the purposes herein, the exemplary methods disclosed in co-pending U.S. patent application Ser. No. 10/115,336 (U.S. Patent Application Publication No. 2003/0183525), entitled "Apparatus and Method for Using Electrostatic Force to Cause Fluid Movement", incorporated herein by reference, will be briefly described. To reduce complexity of the system and to increase reliability, this example drop merging method utilizes electrostatic forces generated by a planar configuration of two electrodes to merge the two drops and cause equilibration through fast mixing. The electrodes can be thin conducting films produced on the surface of the device using microfabrication or other techniques, such as printed circuit board fabrication techniques.

Figure 6:
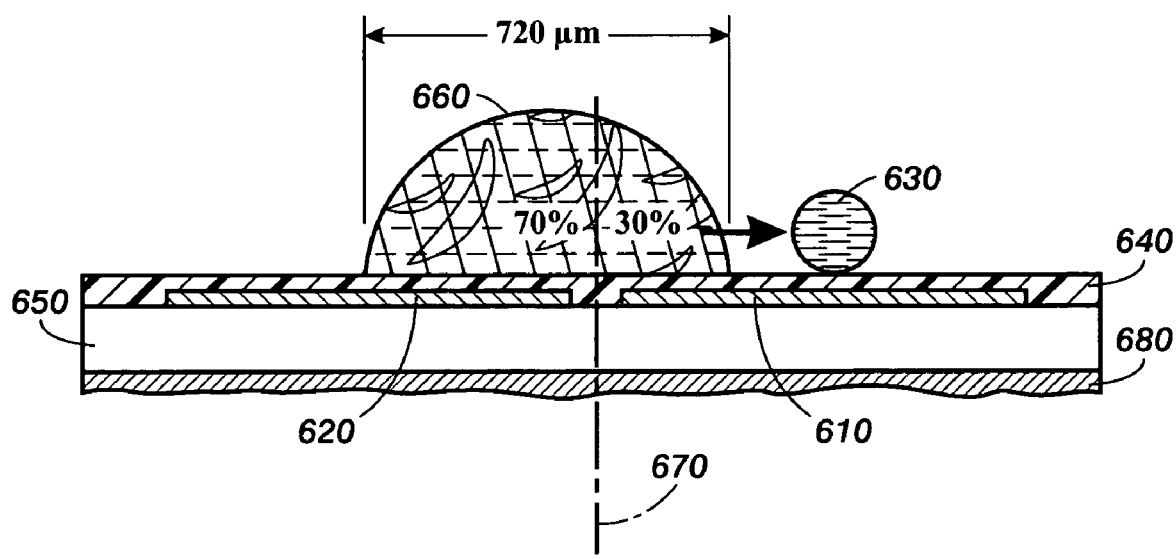
FIG. 6 is a schematic cross-section showing merging of deposited drops on a nanocalorimeter, such as in one of FIGS. 1-4.

FIG. 6 shows merging electrodes formed from conducting films 610 and 620, which are positioned on the surface of substrate 650 and covered by insulating layer 640. In this example, conducting films 610 and 620 may be approximately 1.0 mm by 0.8 mm in size, with a thickness ranging in size from approximately 0.1 μm to approximately 10 μm, and are separated by a gap of approximately 50 μm and are made of a thin film of aluminum, copper, chromium, titanium-tungsten (TiW), or a combination of them; the insulating layer may be approximately 0.1 μm to approximately 2 μm in thickness and may, for example, be made of silicon oxide or silicon nitride or silicon oxynitride, or spin-, spray-, or otherwise deposited polymers, such as parylene, Dupont Teflon® AF, 3M™ Fluorad™ products, 3M™ EGC 1700, other fluoropolymers, polysiloxanes, diamond-like carbon or other spin-coated, spray-coated, dip coated, or vapor deposited polymers. Suitable insulator materials have a high electrical resistivity, chemical and mechanical durability and have no pinholes in deposited thin film form. High conductance film 680 enables thermal equilibration in the thermal equilibrium region. Protein drop 660 is deposited asymmetrically across the surface above conducting films 610 and 620 such that the drop disproportionately occupies the surface above one of the conducting films. In this example, 70% of protein drop 660 occupies the surface on the side of meridian 670 above conducting film 620 and 30% of protein drop 660 occupies the surface on the side of meridian 670 above conducting film 610.

Ligand drop 630 is deposited on the surface above conducting film 610. When a voltage is applied, such as in the form of a voltage pulse, across conducting films 610 and 620, drop 660 is propelled toward stationary drop 630 and the drops merge. While the comparative drop sizes of protein drop 660 and ligand drop 630 may be equal, unequal drop sizes may also be used. The hydrophobic surface of insulating layer 640 minimizes the adhesion of drops 630 and 660 to the surface, which reduces the drag on the drops during merging. In this example, the hydrophobic surface is made of a fluorinated polymer, such as, for example, 3M™ Fluorad™, Dupont Teflon® AF, 3M™ EGC-1700, or plasma-deposited fluorocarbons. In one implementation, a parylene coating may be used as the insulator layer, as well as for the hydrophobic surface.

Alternatively, the thermometer material (e.g. amorphous silicon) itself may be utilized to construct drop mover electrodes. Also, the electrodes and thermometer may be fabricated in different layers, with the electrodes in a layer between the drop deposition points and the thermometer, to enable placing metal drop mover electrodes on top of the thermometers. In this approach, an electrically insulating layer separates the thermometers and electrodes.

The parent application, incorporated herein by reference, describes several available technologies for drop delivery, including syringes and other types of dispensers and techniques such as pin spotting.

Figure 7:
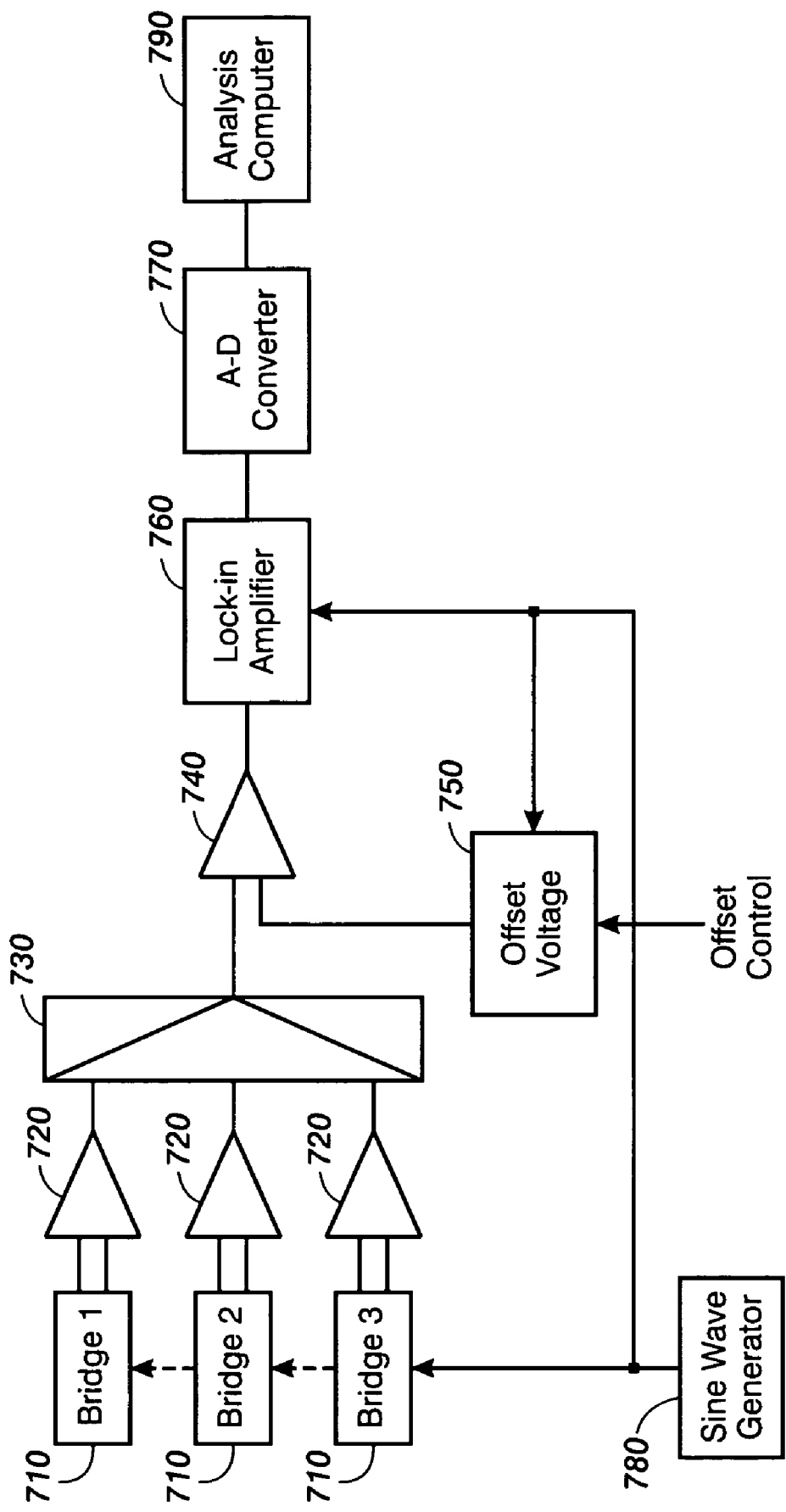
FIG. 7 is a schematic diagram of a second electronic measuring system.

FIG. 7 shows a schematic of a second implementation of an electronic measuring system. For the purposes of example, an alternating current (AC) detection method is illustrated. The AC detection method eliminates the 1/f noise inherent in electronic devices, in which the 1/f noise can be significant at frequencies up to 1 kHz. A bridge circuit is used to detect changes in the resistance of the thermometers. The electronic circuitry implements four functions: amplification of the output of the bridge, zeroing of the bridge, detection of the signal, and computer analysis of the signal. To each bridge 710, a sine wave is provided by generator 780. This sine wave drives the two input terminals of each bridge.

Each bridge has two output terminals whose difference represents the temperature difference of the reference and measurement cells of the bridge. The signal on these two terminals is amplified by a low-noise signal amplifier 720. Because the signal level is low, noise introduced by this function must be minimal, but noise minimization must be balanced by design considerations. For example, for the array to be disposable, which is desirable in some applications, the amplifiers must be located off the array, but amplifiers placed on the periphery result in the introduction of noise through the longer lead length. To minimize noise from interconnect, the amplifiers may be placed on a separate temperature-controlled heat sink positioned in close proximity to the detector array, with amplifiers 720 placed directly above the detector array and contacting the array through compressible pogo-pin connectors. An additional advantage of placing each amplifier directly above its associated bridge is that the bridge output signal wires do not have to pass near any other wires, and thereby avoid noise coupling.

A multiplexer 730 enables several individual detectors to use one lock-in amplifier 760 and analog-to-digital (A-D) converter 770. With the implementation shown in FIG. 7, advantage is derived by the use of one signal amplifier for each detector and placement of multiplexer 730 after the amplifier. The noise introduced by the multiplexer contributes a smaller relative amount than if the multiplexer had been placed before the signal amplifier. Alternatively, if noise levels permit, the multiplexer could be placed before the signal amplifiers, allowing fewer signal amplifiers and a more compact arrangement of amplifiers and bridges.

The temperature sensors in each bridge may be similar but not identical with each other. After temperature equilibration, the output of the bridge will not quite be zero because of these differences. The output will be a small sine wave proportional to the difference. This common mode signal, if not reduced, limits the amount of amplification between the bridge and lock-in amplifier 760. This in turn limits the system sensitivity. The common mode signal is minimized by a bridge zero operation performed after the initial amplification through second stage amplifier 740, which also receives a signal from offset voltage source 750. An offset control signal to source 750 selects a proportion of the sine wave reference signal to be subtracted out of the amplified input signal. This control signal is set by measuring output after equilibration and then setting it to minimize the common mode output. If the inherent balance of the bridge is sufficient, the offset amplifier is not needed.

Lock-in amplifier 760, which produces DC output indicating amplitude of the detector signal, may be implemented with known lock-in amplifiers or equivalent circuitry. Alternatively, the lock-in operation could be implemented in software. In general, a lock-in amplifier can be used to measure signals buried in noise. A lock-in amplifier does this by acting as a narrow bandpass filter that removes much of the unwanted noise while allowing the signal being measured to pass through.

A standard lock-in amplifier known in the art includes a variable gain input amplifier that increases input signal amplitude; a phase detector; and a low-pass filter with adjustable cut-off frequency. The lock-in amplifier receives an input signal with an unknown value and a reference sine wave at the frequency of modulation of the signal being measured. After input amplification, the input signal is mixed with the reference signal (this operation is also known as phase detection) and then sent through the low-pass filter. This low-pass filtering effectively removes substantially all electronic noise that is picked up between the source (in this case, the Wheatstone bridge) and the output. The DC-coupled output signal of the lock-in amplifier is proportional to the amplitude of the input signal.

The analog output of the lock-in operation is digitized by A-D converter 770 (conventionally included within lock-in amplifier 760, providing a digital output signal) and can be input into computer 790 for analysis. Amplitude of the digitized signal represents temperature difference on the bridge. After the drops are moved together and when a reaction occurs, the amplitude will increase until the drops are fully mixed and then decrease as heat is removed through conduction and evaporation. If no reaction occurs, no significant change will occur in the amplitude. The computer can correlate the digitized signal against expected temperature increase and decrease. If the correlation is positive, then the occurrence of a reaction is signaled.

Figure 8:
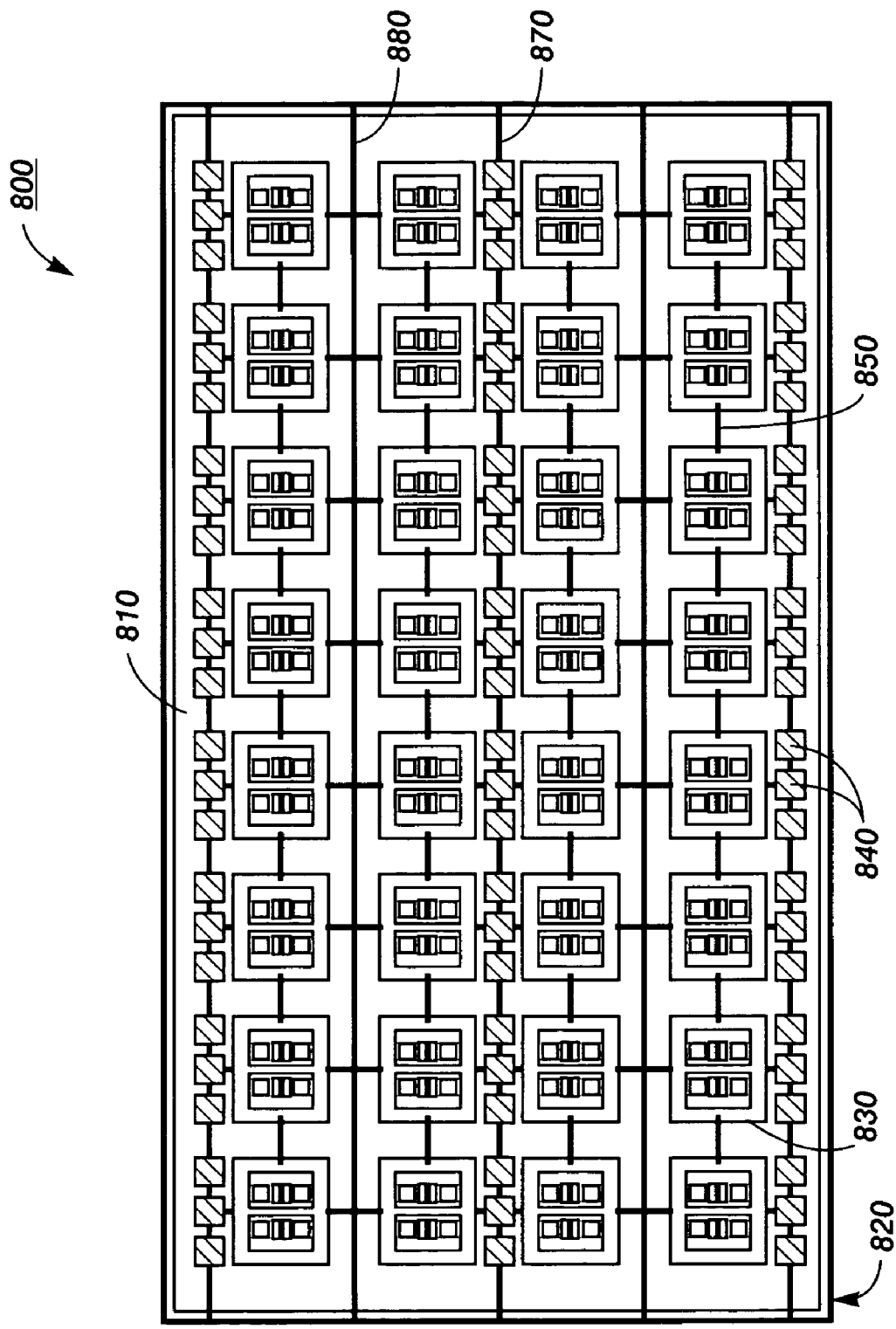
FIG. 8 is a top plan view of an array of components of a nanocalorimeter that can be used with the system of FIG. 7.

FIG. 8 shows detectors of a detector array arranged in a rectilinear orientation to form a matrix array. In this example, the array is fabricated on thin plastic sheet 810, for example a 12-24 μm thick Kapton® plastic substrate, and is supported by heat sink 820, which is made of a material with a high thermal conductivity such as Cu or Al. Thin film conducting lines 850 placed in the regions between individual detectors 830 serve as electrical interconnect that carry signal and power between the detectors and the electronic module on the outside. Detectors 830 require interconnect for signal excitation and drop merging electrodes. All detectors in pairs of adjacent rows are connected to common merge-electrode power 880.

The resistive thermometers, drop merging electrodes, and electrical interconnect may be patterned on one side of the matrix array, and the thermal equilibration film may be fabricated on the other side. Measurements can be made simultaneously in two rows. Detector signal and ground are provided through contact pads located over the heat sink adjacent to each detector and connected to the array through detector amp contact pads 840. Common bridge-excitation is provided for pairs of rows by bridge power conducting lines 870. The merge-electrode power and common bridge-excitation are introduced through alternating rows. Because it is desirable to transfer fluids from standard storage devices, such as well-plates having different densities (96 well, 384 well, or 1536 well) the detectors have the same 9 mm square layout as standard 96 well-plates used in the biotechnology and pharmaceutical industries.

If implemented with resistive thermometer elements that include vanadium oxide, the array of FIG. 8 thus illustrates an example of an array with calorimeters, each including a set of resistive thermometer elements that include vanadium oxide. Each calorimeter also includes circuitry through which electrical resistance of the thermometer elements can be detected. Each calorimeter also includes a structure with a reaction region in which reactions that produce thermal change occur.

The structure conducts temperature from reactions in the reaction region to at least one of the thermometer elements.

The above-described techniques for producing the array of FIG. 8 also illustrate an example of a method of producing a calorimeter with the above features.

Figure 9:
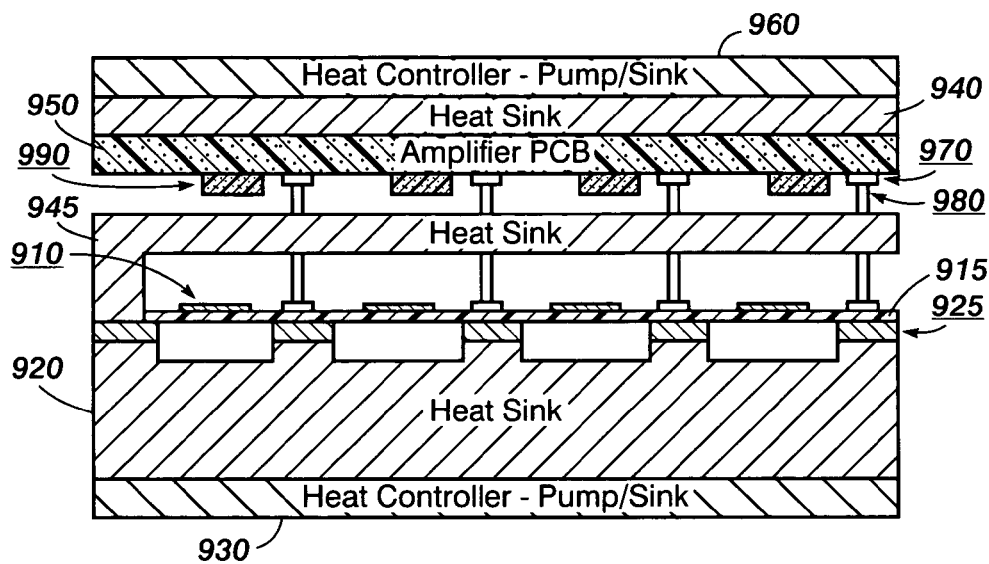
FIG. 9 is a cross-sectional diagram illustrating the operating environment of a nanocalorimeter as in FIG. 8.

FIG. 9 shows a cross-section of the nanocalorimeter assembly and its detector environment, which provides thermal isolation, electrical connections and sample delivery. To achieve thermal isolation, the environment is structured to insure that the heat transferred to or from the drop is minimized to a value as close to zero as possible; one technique employs a cap over a sensing region, as described below in relation to FIG. 19 of copending U.S. patent application Ser. No. 11/167,746 entitled "Thermal Sensing" and incorporated herein by reference; another approach is to perform signal processing on resulting data to correct for heat transfer. The three main heat transfer channels for the assembly include: thermal conduction through the air, thermal conduction across the supporting medium, and evaporation, with evaporation being much larger than the others.

To reduce evaporation to acceptable limits, measurements can be conducted at low temperatures and high humidities, for example 5° C. in near 100% relative humidity (e.g. non-condensing). Specifically, evaporation is controlled in part by maintaining near 100% relative humidity, within some acceptable tolerance, of the solvent used to dissolve the chemicals being investigated. This may be accomplished by exposing a reservoir of solvent to the atmosphere in the chamber enclosing the detector. The lower temperature reduces the vapor pressure of the solvent, and higher humidities reduce the concentration gradient of solvent in the gas phase near the surface of the drop, thereby reducing the driving force for evaporation. In other implementations, reasonable measurements might be attainable at higher temperatures or lower humidities despite the correspondingly higher evaporation rates, in which cases operation at low temperatures or high humidities may not be necessary.

Thermal conductivity through the surrounding environment can be reduced through use of a controlled atmosphere, for example an environment rich in xenon or argon, which have lower thermal conductivities than air. Conductivity can also be controlled through the use of a partial or complete vacuum, aerogels or other insulating materials, and other methods that will occur to those skilled in the art.

To minimize thermal conduction across the supporting medium, detector 910 resides on substrate 915, which is supported by substrate carrier 925, which is in contact with heat sink 920. In this example heat sink 920 is comprised of copper, but other materials known in the art could also be utilized. Heat sink 920 may be in thermal contact with an optional active temperature control device 930, which controls the temperature of the heat sink to within 1 mK to 0.1 K of amplifier heat sink 940.

The detector amplifiers dissipate power (10 mW each), which may be too much heat for the detector heat sink in some implementations. The amplifier power can be sunk to a separate heat sink if desired. Signal amplifiers 990 reside on amplifier printed circuit board (PCB) 950, which is in contact with heat sink 940. The temperature of heat sink 940 can be controlled by a temperature control device 960, if desired for a particular implementation. Pogo-pin connectors 980 connect amplifier PCB 950 with detector substrate 915 through amplifier pads 970.

There are several conditions in which the heat sink 920 does not need to be temperature controlled. In these cases, the heat sink is thermally isolated from the enclosing chamber using standard low conduction materials like glass, plastic or stainless steel tubing. In these cases, the amplifier PCB 950 is placed in direct contact with the temperature controlled enclosing chamber.

Tables 3 and 4 and the related description in the parent application, incorporated herein by reference, illustrate the magnitude of temperature fluctuations that heat sink 920 may experience.

Figure 10:
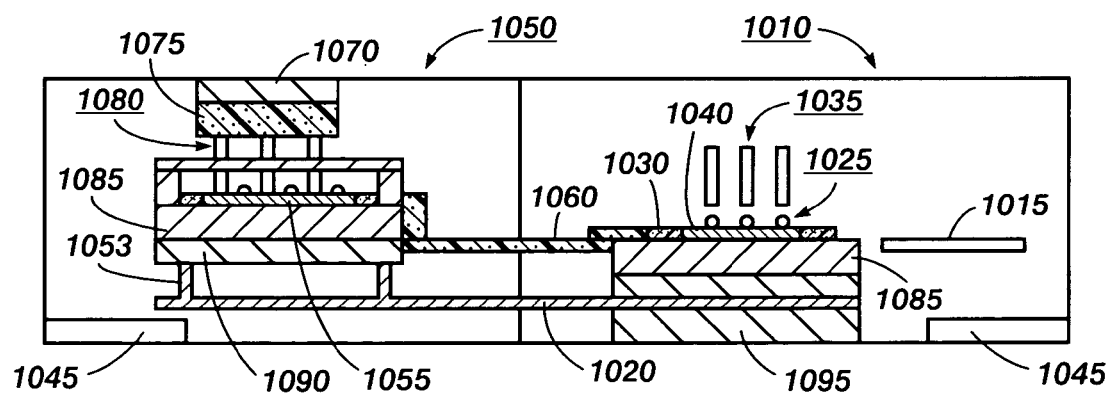
FIG. 10 is a cross-sectional diagram illustrating an implementation of process flow of a nanocalorimeter as in FIG. 8.

FIG. 10 illustrates a cross section of a measurement system utilizing the array described above. The measurement system in this example configuration includes two compartments, load lock chamber 1010 and measurement chamber 1050. The chambers and the atmosphere contained within them are equivalent; they are at the same operating temperature. The atmosphere within each chamber is a non-reactive gas, for example xenon, argon, air, or nitrogen, at a near 100% relative humidity for the solvents used in the drops being measured, and this humidity level is maintained through use of vapor pressure reservoirs 1045. The temperature of the chamber walls is controlled to within 0.1 K. Heat sink 1085, mounted on heat conductor 1090, receives heat from the power dissipated in the measurement thermometers on detector array 1040 when in the measurement chamber 1050. In this example four thermometers are used for each detector, as shown in FIG. 1, and each thermometer dissipates approximately 4 μW. The rate of temperature increase of heat sink 1085 due to thermometer heating is approximately 10 μK during a 10 second measurement, based on a 96 detector array and a heat sink with a heat capacity of 1500 J/K (refer to Table 3 above). Detector array 1040 is connected to detector array electronics 1030 which in turn are connected to system electronics 1060. Biomaterials are contained within a biomaterial storage well plate 1015, which is placed in the load lock chamber 1010. In the measurement chamber 1050 are detector electronics 1075 as well as the associated heat sink/controller 1070 for the detector electronics.

Biomaterials 1025 are deposited on the array with chemical deposition device 1035 in preparation for the measurement. While in the load lock chamber 1010, the heat sink 1085 and associated detector 1040 and biomaterials 1025 are brought into thermal equilibrium with the chamber through heat conductor 1095. Heat conductor 1095 may be any material or system of high thermal conductivity, and may be, for example, a metal block such as copper or aluminum that is in good thermal contact with both the chamber wall and the heat sink 1085. As shown in FIG. 10, thermal contact of heat conductor 1095 with heat sink 1085 occurs through the array transporter 1020. However, this configuration is exemplary only; other configurations will occur to those skilled in the art and are contemplated by the disclosure herein.

In alternative implementations, heat conductor 1095 may have active temperature control, such as control by a circulating-fluid refrigeration or heating system, a Peltier device, a resistive heater, a heat pump, or any of a number of other active temperature-control devices known by those skilled in the art. Furthermore, the heat conductor and associated temperature control function can be integrated into the array transporter 1020. Array transporter 1020 moves a detector array with deposited biomaterials from the load lock into measurement chamber 1050 and, in this example, utilizes a circular motion so that a detector array with measured materials is simultaneously moved from the measurement chamber to the load lock. Other array transport methods may be utilized, such as pick-and-place devices and belt devices with elevators.

Once in the measurement chamber, the detector array is raised into contact with the pogo pins, and simultaneously the heat sink 1085 (with heat conductor 1090) is raised above the transporter 1020 and thermally isolated from it by supporting pins 1053. The supporting pins may be fabricated from any good thermal insulating material with sufficient mechanical strength, such as glass rods, stainless steel hollow tubing, plastic rods, porous ceramics, and other materials known to those skilled in the art. Other configurations are possible; for example, a temperature controller may be used to maintain heat sink 1085 at a specified temperature in measurement chamber 1050, for example within 1 mK of the temperature of heat sink/controller 1070 of detector electronics 1075, rather than relying on thermal isolation alone. Pogo-pin detector connectors 1080 make electrical contact directly to the detectors to transmit thermal change information from the detector array to detector electronics 1075. This type of connector is used in this example to provide a nonpermanent connection that allows connection to be made to successive arrays with low thermal contact to the array and good placement accuracy with a small foot-print that provides symmetrical contact to the measurement and reference regions to enable precise differential measurements.

In operation, detector array 1040 is placed in load lock chamber 1010 while a previously set-up detector array 1055 is being measured in measurement chamber 1050. The initial temperature of detector array 1040 could, for example, be within 1 K of the temperature of load lock chamber 1010, or measurement could be timed to avoid this and other temperature constraints. The proximity of measurement chamber 1050 to load lock chamber 1010 enables the connected detector array to be moved between the chambers while remaining in a controlled environment. Biomaterials are then moved into load lock chamber 1010 and stored in an appropriate vehicle 1015, such as a 384 or 1536 well plate, although other containers or well plate sizes would also be appropriate. Biomaterials 1025 are then deposited on detector array 1040 using, for example, an aspirating/printing system or an automated syringe-type loader 1035. Deposition device 1035 is maintained at a controlled temperature to avoid warming biomaterials 1025. Initially, detector array 1040 is connected to detector array electronics 1030 and system electronics connector 1060, which provides the necessary electrical connections to all the detector elements in detector array 1040 with the exception of the detector electronics for the measurement bridge. Depending on conditions, the detector bridges in detector array 1040 may be driven by the AC sine wave (for example, element 560 in FIG. 5) to self-heat to a temperature that equilibrates the drop temperature with the controlled environment in the load lock chamber. This signal is conducted through the system electronics connector 1060 to the detector array electronics 1030.

After the deposited materials 1025 come to thermal equilibrium with the detector array 1040, the detector array 1040 with deposited chemicals 1025 is then moved from load lock chamber 1010 to measurement chamber 1050 by array transporter 1020 and measured detector array 1055 is moved into load lock chamber 1010. This movement may be accomplished through a rotation, such as a 180-degree rotation, or by any other means known in the art. Within measurement chamber 1050, the detector array is in thermal contact with heat sink 1085, which in this implementation is thermally isolated from transporter 1020 by supporting pins 1053 in measurement chamber 1050. The measurement sequence is initiated by applying the AC sine wave to the detector bridges. This signal is created by an AC generator located on the amplifier PCB 1075 and conducted to detector array 1055 through the pogo pins 1080. The detector bridge is then zeroed by properly setting the offset voltage. Thermal equilibration is confirmed by measuring the voltage across the detector bridge for a short period of time. When the rate of change of this voltage is below a pre-specified level, the system is in thermal equilibrium. The zeroing operation may need to be repeated during this process.

A row of drops of deposited chemicals 1025 is then merged and mixed on the surface of the detector array. This is accomplished by applying a drop moving voltage from the amplifier PCB 1075 through the pogo pins 1080 to the detector array 1055. The transient voltages generated from the merging voltages are allowed to dissipate. The reaction during mixing is then measured by detecting the imbalance in the bridge. Each bridge in the row is measured repeatedly for a period of time and the data is input into the computer for analysis.

The individual bridges in a single row may be multiplexed in the detection electronics. A measurement is made on one detector and then the next detector in the row until all the detectors in the row have been measured. This is repeated for a period of time until all measurements for the row are complete. Alternatively, multiple instances of the detection electronics can simultaneously measure all the detector arrays in the row. To further reduce measurement time, measurements may be performed in blocks of two or more rows.

Figure 11:
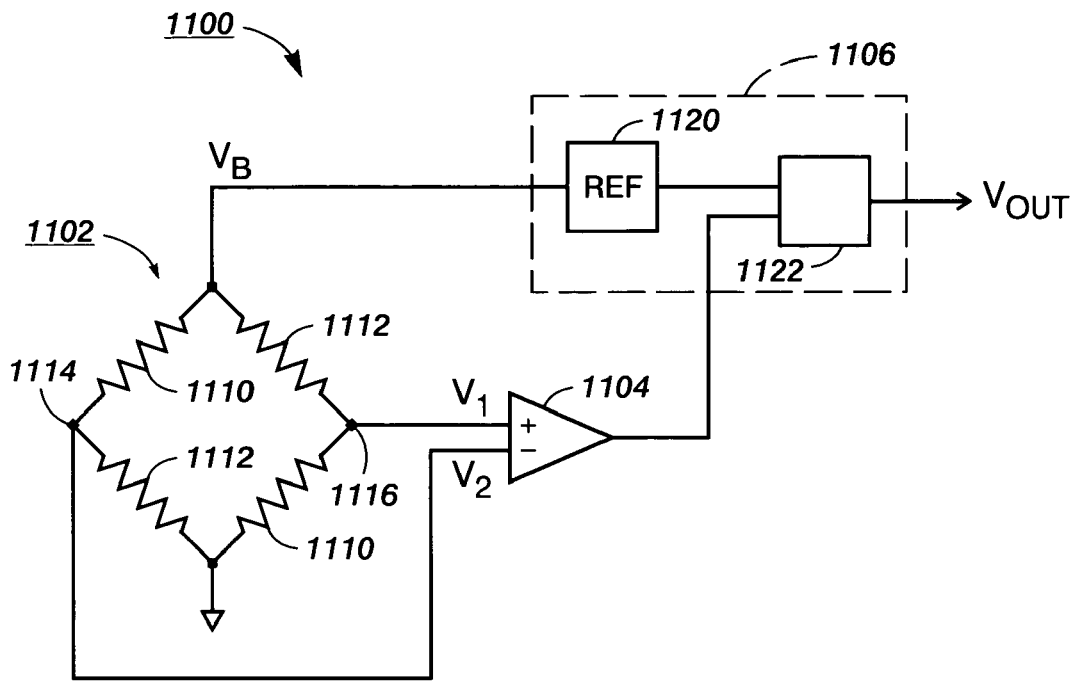
FIG. 11 is a schematic diagram of a third electronic measuring system that includes resistive thermal sensors.

FIG. 11 is a schematic diagram of an electronic measuring system similar to that shown in FIG. 5, but with different details. Measuring system 1100 includes thermistor bridge 1102, instrumentation amplifier 1104, and lock-in amplifier 1106.

The term "thermal input signal" refers herein to a signal provided to a component in the form of thermal change, and the thermistors in thermistor bridge 1102 receive different thermal input signals. Thermistor bridge 1102 includes two pairs of opposite thermistors, arranged in a Wheatstone bridge that suppresses, to the first order, common-mode variations, i.e. variations in output signal as a result of common variations in resistance of all the thermistors. Implementations of bridge circuitry and related techniques are described in greater detail in co- pending U.S. Patent Application No. 11/167,612, entitled "Thermal Sensing With Bridge Circuitry" an reference in its entirety.

Thermistors 1110, referred to as "measuring thermistors," are located so that they are exposed to a thermal input signal that is being measured, while thermistors 1112, referred to as "reference thermistors," are located to make a reference measurement. For example, if the thermal effect of a reaction is being measured, thermistors 1110 can be located so that a thermal signal indicating heat from the reaction would be conducted or otherwise provided to them, while thermistors 1112 can be located away from and insulated from the reaction so that they receive no such thermal signal.

Instrumentation amplifier 1104 amplifies the difference voltage between nodes 1114 and 1116 of bridge 1102 and can be implemented as a low-noise, very high impedance amplifier. Its output is provided to lock-in amplifier 1106, which performs second stage amplification, removing additive voltage noise by bandwidth narrowing. The voltage $V_B$ provided to bridge 1102 is a sinusoidal voltage derived from the internal reference voltage source 1120 of lock-in amplifier 1106. Lock-in amplifier 1106 also includes an amplifying component 1122 that receives the reference voltage and the output from instrumentation amplifier 1104 and provides the output signal $V_{out}$. $V_{out}$ is proportional to the difference between the temperature sensed by the measuring thermistors 1110 and the temperature sensed by the reference thermistors 1112.

The circuitry in FIG. 11 can generally be implemented with standard electrical components, except that bridge 1102 includes thermistors with particular noise properties under a device's operating conditions. For example, they can be low noise thermistors or they can be thermistors that include materials with specific noise characteristics. In a low noise implementation, instrumentation amplifier 1104 and other resistors (not shown) would also be selected for low noise characteristics under the device's operating conditions. The term "operating conditions" is used herein to refer to the relevant conditions under which a calorimeter or other thermal sensing device is designed to operate, such as dissipated power, bias voltage, ambient temperature, and so forth.

As used herein, a "low noise thermal sensor" is a thermal sensor for which the noise equivalent temperature difference (NETD) is not greater than approximately 50 µK over a typical thermal sensing bandwidth range of approximately 3 Hz or more under a device's operating conditions; a typical thermal sensing bandwidth range is 0.1 Hz to 4.2 Hz, for example, and a bandwidth range of 1 Hz to 4.2 Hz is also useful in some situations. NETD of a thermal sensor refers herein to the apparent temperature difference between an object and its surroundings that produces an effect equal to the intrinsic noise of the sensor; it could also be described as the differential temperature at which the signal to noise ratio of the sensor is unity. A "low noise thermistor" is accordingly a thermistor that can be used in a low noise thermal sensor.

Also, a thermistor that does not fall precisely within the above definition of a low noise thermistor could be advantageously used in bridge 1102. For example, if bridge 1102 includes thermistors with vanadium oxide (VO$_x$) deposited at room temperature, bridge 1102 can easily have NETD not greater than approximately 100 µK over a thermal sensing bandwidth range of approximately 3 Hz or more under a calorimeter's operating conditions; as described in greater detail below, VO$_x$ thermistors have been fabricated and included in thermal sensors with NETD not greater than approximately 35 µK or even 10 µK over a bandwidth range of 1 Hz to 4.2 Hz under appropriate operating conditions. This is advantageous because deposition of VO$_x$ at room temperature is consistent with fabrication on substrates such as low temperature plastics that are not readily compatible with the temperatures necessary for PECVD deposition of amorphous silicon, a frequently used thermistor material.

In general, resolution of a temperature measurement made by system 1100 in FIG. 11 is limited by several factors: Thermistor noise; contact noise, such as from pogo pin contacts or other contacts; other electrical noise, such as from the amplifiers; TCR of each thermistor; maximum bridge supply voltage $V_B$ allowed; and limits in the common-mode rejection ratio of the Wheatstone bridge. By performing a noise analysis on an implementation of system 1100, it is possible to optimize electrical components for noise. For example, lock-in amplifier 1106, with a reference frequency typically around 1000 Hz, suppresses most of the 1/f (low frequency) noise originating from the electronics itself or the environment.

The amplifier portion of system 1100 can also be empirically calibrated by connecting it to dummy metal film resistor bridges, in which case the measured noise lies close to the theoretical Johnson noise, also known as thermal noise, i.e. the theoretical minimum achievable noise level; specifically, the measured noise in such a setup is typically a factor of 2 greater than the theoretical Johnson noise. Actual measurements of contact noise from pogo pin contacts indicate that this noise does not play a significant role at current noise levels, though it might if even lower noise levels can be achieved. Maximum bridge supply voltage $V_B$ is limited by self-heating and by the input range of instrumentation amplifier 1104. More specifically, offset arises because the thermistors in bridge 1102 are not ideally matched, and the offset causes limited common-mode rejection through differential self-heating, as well as causing amplifier input range limitations. Small thermal imbalances and fluctuations between measuring thermistors 1110 and reference thermistors 1112 also limit common-mode rejection and measurement resolution because they result in erroneous signals.

After optimizing other components for noise, it is still possible to obtain further improvement by optimizing thermistors 1110 and 1112, both for noise and for TCR. Both noise and TCR of the thermistor material affect the NETD of the thermal sensor, which is used as a figure of merit for the sensor. Assuming that a thermistor's resistance is a linear function of temperature, which is a valid approximation for small temperature variations, and that the four resistors in the Wheatstone bridge are well-matched, the NETD of bridge 1102 can be calculated as follows:

$$NETD = \frac{2 \cdot V_{noise}}{V_{bridge} \cdot TCR} \tag{Eq. 1}$$

where $V_{bridge}=V_B$ in the implementation of FIG. 11 and $V_{noise}$ is an observed noise voltage at nodes 1114 and 1116.

Figure 12:
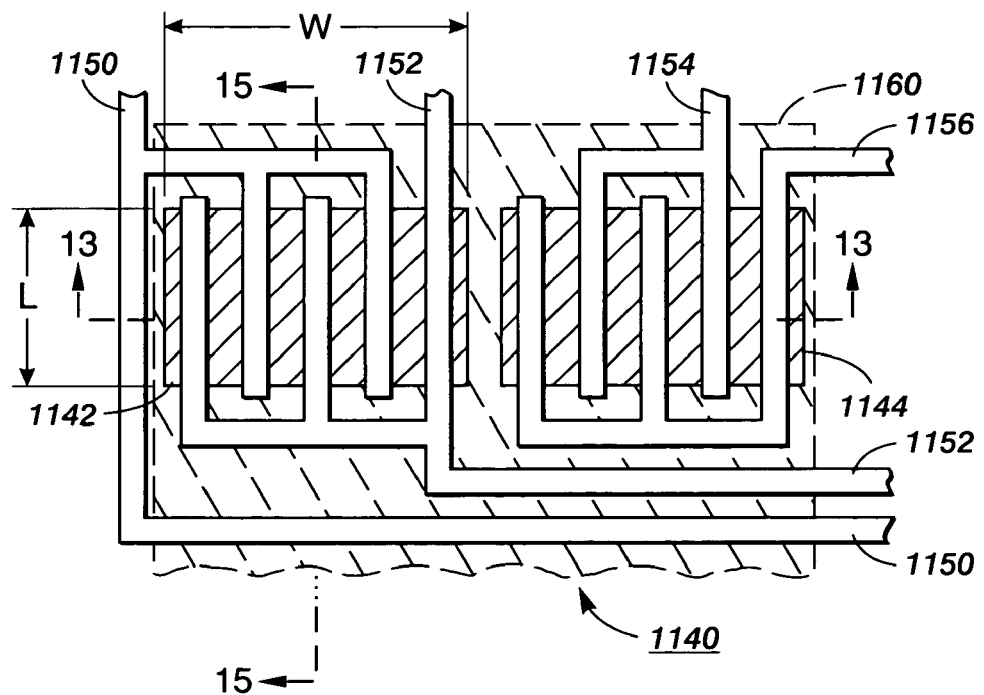
FIG. 12 is a top plan view of a pair of low noise resistive thermal sensors that can be used in the system of FIG. 11.

FIG. 12 shows a top plan view of a pair of thermistors 1140 that can be used in bridge 1102 in FIG. 11, either thermistors 1110 or thermistors 1112. Each thermistor includes a rectangular slab of thermistor material, with slab 1142 being on the left in FIG. 12 and slab 1144 on the right. Each slab has dimensions W and L, which are illustratively shown for slab 1142, and the dimensions of slab 1144 are substantially identical. Leads 1150 and 1152 have interdigitated lines that extend across slab 1142, while leads 1154 and 1156 have interdigitated lines that extend across slab 1144. On the opposite side of layer 1162 from slabs 1142 and 1144 is thermally conductive component 1160, which extends to an adjacent region at which it is exposed to the temperature either of a reaction or a reference. When the reaction occurs within a fluid drop under control of drop merging electrodes, component 1160 thermally couples the drop with slabs 1142 and 1144, providing a thermally conductive path from the drop to thermal sensors that include slabs 1142 and 1144.

Figure 13:
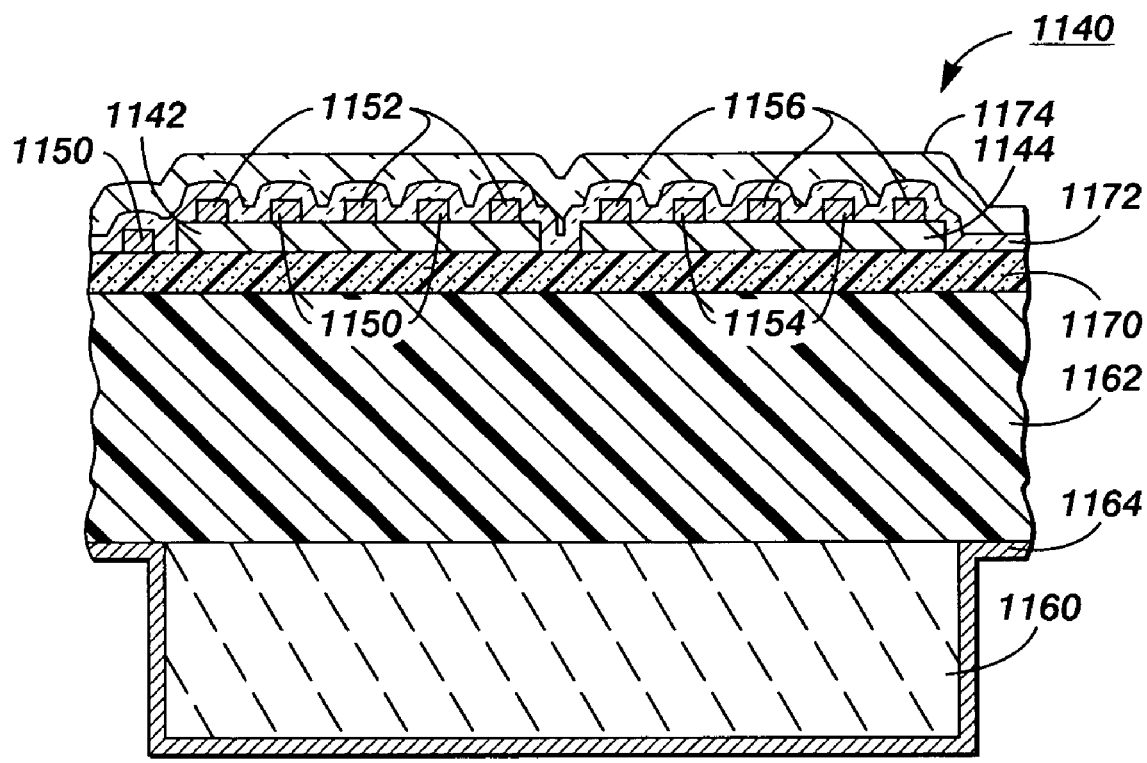
FIG. 13 is a cross section of the pair of thermal sensors, taken along line 13-13 in FIG. 12.

FIG. 13 shows thermistor pair 1140 in cross-section along the line 13-13 in FIG. 12. Polymer layer 1162 can, for example, be a 1 mil (25.4 µm) thick polyimide layer, such as Kapton® film from DuPont, on which other components are microfabricated in a manner described in greater detail below in relation to FIG. 15. Polymer layer 1162 provides thermal isolation between thermistor pair 1140 and other components, and, for this purpose, any other suitable thermally isolating film could be used instead of polymer, including inorganic materials.

Thermally conductive component 1160 is on the lower surface of polymer layer 1162, and can include thermally conductive metal such as copper or aluminum at a thickness of 9 µm or thinner; in general, component 1160 can include any thermally conductive material and desired conduction can be obtained by adjusting thickness in proportion to the material's thermal conductivity.

Deposited over thermally conductive component 1160 is anti-coupling layer 1164, which could be implemented as a 10 nm thick layer of gold, and functions to prevent capacitive coupling between adjacent parts of thermally conductive component 1160; because it is very thin, layer 1164 has low thermal conductivity, preserving thermal isolation. Layer 1164 is believed to reduce noise by coupling component 1160 to ground, preventing slabs 1142 and 1144 from capacitively accumulating additional charge that could affect their response to thermal input signals. Implementations of layer 1164 and of other applicable anti-coupling measures are described in greater detail in co-pending U.S. patent application Ser. No. 11/167,746, entitled "Thermal Sensing" and incorporated herein by reference in its entirety.

On the upper side of polymer layer 1162, barrier layer 1170 protects against contaminants and humidity, increasing device performance; barrier layer 1170 has been successfully implemented with a layer of approximately 300 nm of silicon oxynitride ($SiO_xN_y$). Slabs 1142 and 1144 are on barrier layer 1170, and include material making it possible for thermistor pair 1140 to be low noise thermistors, as discussed in greater detail below. Leads 1150, 1152, 1154 and 1156 are on slabs 1142 and 1144 and, in places, on barrier layer 1170; leads 1150 can be implemented, for example, with a suitable conductive metal sandwich such as Cr/Al/Cr or TiW/Al/Cr to provide electrical contact with slabs 1142 and 1144 and to provide conductive paths to other circuitry discussed in greater detail below.

Additional layers deposited over leads 1150, 1152, 1154, and 1156 provide electrical passivation, environmental barriers, and hydrophobic surfaces, which are especially useful for a system in which temperature of reactions between fluids are measured through drop deposition and merging. In FIG. 13, these layers illustratively include protective layer 1172 and polymer layer 1174. Protective layer 1172 can be produced by plasma-enhanced chemical vapor deposition (PECVD) of silicon oxynitride, while polymer layer 1174 can include a layer of parylene to provide a barrier to liquid and to electrical leakage and to provide some hydrophobicity. Fluorocarbon polymer can be dip coated over the parylene to obtain a more hydrophobic surface. Alternatively, polymer layer 1174 could include a Teflon® coating from DuPont or a similar material.

Figure 14:
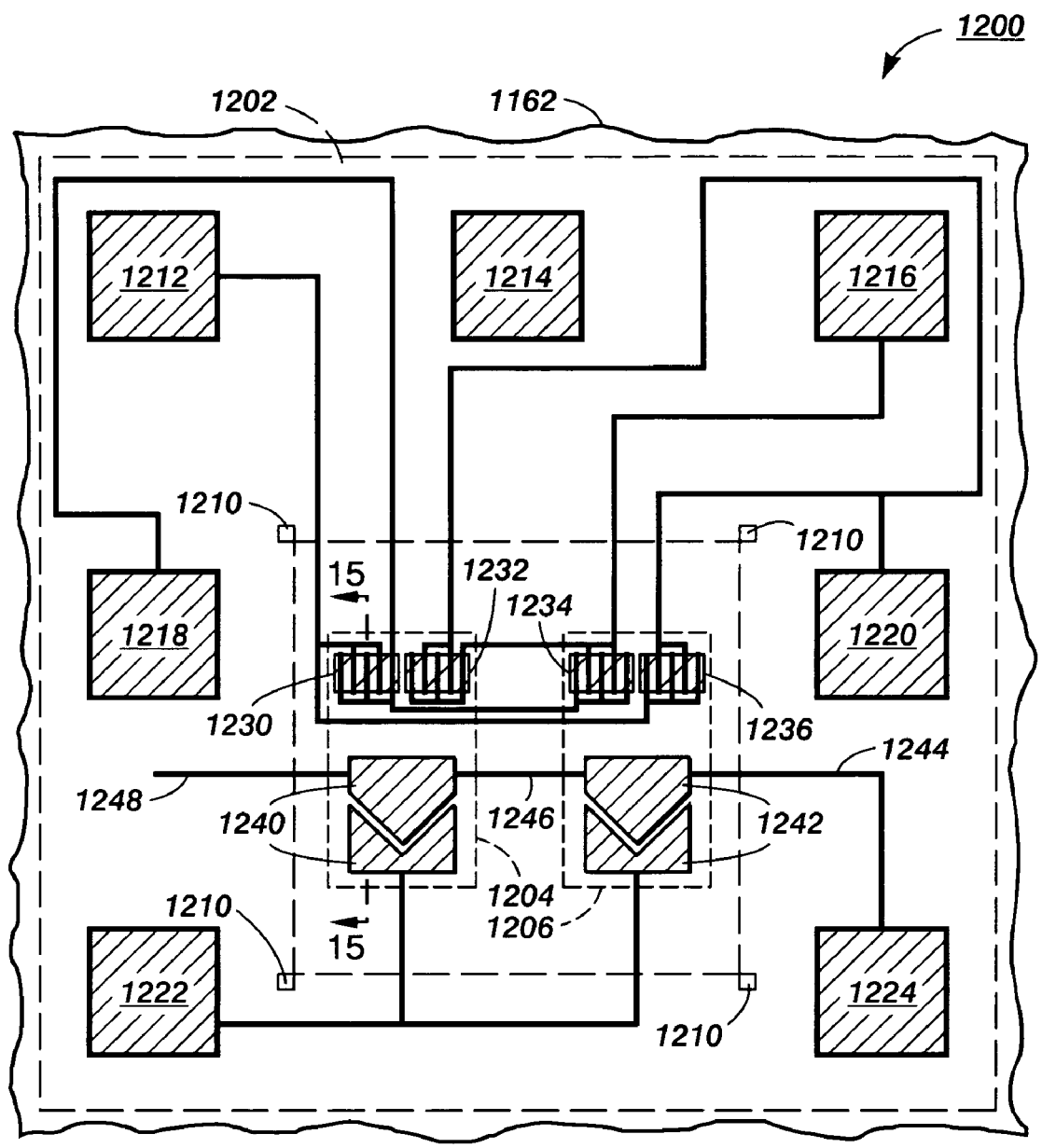
FIG. 14 is a partially schematic top view of a thermal sensing cell that includes two pairs of thermal sensors like those of FIGS. 12 and 13.

FIG. 14 illustrates a thermal sensing cell 1200 that includes two pairs of thermal sensors like those shown in FIGS. 12 and 13. Frame 1202 (shown in dashed lines) supports polymer layer 1162 (FIG. 13) from underneath. In addition, islands 1204 and 1206 (shown in dashed lines) are on the underside of polymer layer 1162 and each can be implemented like thermally conductive component 1160 (FIG. 12).

Frame 1202 illustratively has alignment structures 1210 at the corners of a recess within which islands 1204 and 1206 are positioned. Frame 1202 can, for example, be formed from 1 mm thick stainless steel in which alignment structures 1210 and the recess for islands 1204 and 1206 are etched, and the recess can then provide thermal isolation between islands 1204 and 1206 as well as between either of the islands and frame 1202. Thermal isolation could be maintained in various other ways.

Contact pads 1212, 1214, 1216, 1218, 1220, 1222, and 1224 are on the upper surface of polymer layer 1162 over frame 1202. Each contact pad (except contact pad 1214) is connected to one or more of the components over islands 1204 and 1206 by leads that are shown schematically in FIG. 14. If cell 1200 is approximately square with 9 mm sides, the contact pads can be approximately 1 mm×1 mm, allowing connection with pogo pins. The leads can be approximately 50 μm wide or even wider as long as they do not result in loss of thermal isolation.

Thermistor slabs 1230, 1232, 1234, and 1236 can each be implemented as described above for thermistor slabs 1142 and 1144 (FIGS. 12 and 13), providing two thermistor pairs, one with slabs 1230 and 1232 and the other with slabs 1234 and 1236. The contact pads could be connected in various ways to provide an implementation of bridge 1102. For example, voltage $V_B$ can be applied to one of contact pads 1212 and 1216 while the other is connected to ground to provide a Wheatstone bridge with contact pad 1218 connected to one of nodes 1114 and 1116 and with contact pad 1220 connected to the other. Therefore, one of the thermistor pairs includes measuring thermistors 1110 while the other includes reference thermistors 1112, as can be understood by comparing with bridge 1102 in FIG. 11.

The contact pads in FIG. 14 can be electrically contacted with any suitable connectors such as pogo pins, both for controlling drop merger electrodes and for electrically detecting thermal signals in the bridge. With a polymer layer substrate, crossing lines and vias are problematic. The layout in FIG. 14 provides a simpler layout with no crossing lines and with no vias, in part because all circuitry is within the cell's region, and none of the circuitry extends or connects electrically outside the cell's region except through contact pads. This technique also avoids long, unreliable lines that, if broken, could disable an entire row or column of an array.

FIG. 14 also shows drop mergers 1240 and 1242, on one of which a reaction can be caused and differential temperature measurement performed. Drop mergers 1240 and 1242 illustratively have chevron shaped features, but could also be implemented by any of the techniques described in co-pending U.S. patent application Ser. No. 11/018,757 entitled "Apparatus and Method for Improved Electrostatic Drop Merging and Mixing", incorporated by reference herein in its entirety. Conductive line 1244 extends from pad 1224 to the upper part of drop merger 1242, conductive line 1246 extends between the upper parts of drop mergers 1240 and 1242, and conductive line 1248 extends leftward from the upper part of drop merger to provide some symmetry with conductive line 1244. Pad 1222 is connected to the lower parts of both drop mergers. Description of features shown in FIG. 14 that relate to reducing offset voltage are described in co-pending U.S. patent application Ser. No. 11/167,612, entitled "Thermal Sensing With Bridge Circuitry" and incorporated herein by reference in its entirety. Description of features shown in FIG. 14 that relate to providing signals through contact pads and electrical detection through contact pads are described in co-pending U.S. patent application Ser. No. 11/167,635, entitled "Thermal Sensing" and incorporated herein by reference in its entirety.

Figure 15:
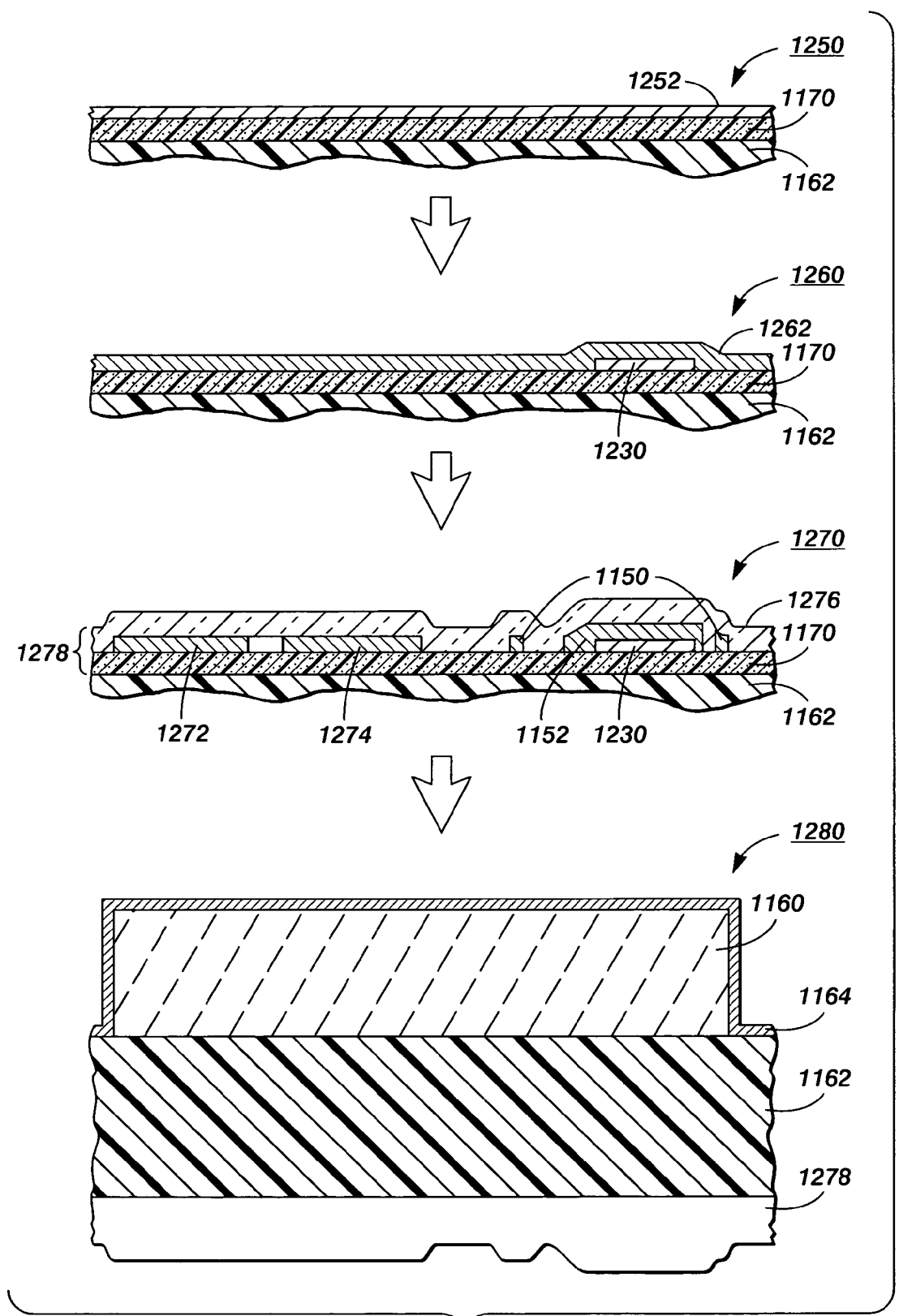
FIG. 15 shows a sequence of cross-sectional views in production of a thermal sensing cell, taken along line 15-15 in FIGS. 12 and 14.

FIG. 15 shows several cross-sections in producing thermal sensing cell 1200, taken along line 15-15 in FIGS. 12 and 14. As can be seen from FIG. 12, line 15-15 extends through the middle digit of lead 1152 where it extends over slab 1142. The operations illustrated in FIG. 15 are similar to those described in Torres, F. E., Kuhn, P., De Bruyker, D., Bell, A. G., Wolkin, M. V., Peeters, E., Williamson, J. R., Anderson, G. B., Schmitz, G. P., Recht, M. I., Schweizer, S., Scott, L. G., Ho, J. H., Elrod, S. A., Schultz, P. G., Lerner, R. A., and Bruce, R. H., "Enthalpy arrays", *Proceedings of the National Academy of Sciences*, Vol. 101, No. 26, Jun. 29, 2004, pp. 9517-9522 ("the Torres et al. article"), incorporated herein by reference in its entirety.

Prior to cross-section 1250 in FIG. 15, polymer layer 1162 is prepared for subsequent operations. As noted above, polymer layer 1162 can be a 1 mil (25.4 μm) or ½ mil (12.7 μm) thick Kapton® film or other polyimide film and is generally held flat during processing, because flatness is important for photolithography and for uniform feature sizes. Prior to deposition of material on polymer layer 1162, the surfaces of layer 1162 are cleaned, and layer 1162 is stretched and mounted by lamination on a frame (not shown). Mounting layer 1162 on a stainless steel frame prevents it from curling or cracking during processing.

Cross-section 1250 shows a portion of polymer layer 1162 on which barrier layer 1170 has been deposited. Barrier layer 1170 has been successfully implemented with a PECVD silicon oxynitride deposited to a thickness of 300 nm, which has been successful in producing a low noise thermistor; other materials may also be suitable, including insulating films such as sputtered $SiO_2$ or PECVD SiO or SiN. When properly deposited, barrier layer 1170 provides improved surface smoothness and a humidity and contamination barrier.

Cross-section 1250 also shows layer 1252 with semiconductor material deposited over barrier layer 1170. As described in greater detail below, layer 1252 could include vanadium oxide ($V_O$), heavily p-doped amorphous silicon, or other material suitable for low noise thermistors. As used herein, amorphous silicon is referred to as "heavily p-doped" if it includes a p-dopant that provides approximately the same carrier concentration as would result from doping with boron atoms by introducing diborane gas into a PECVD reaction chamber together with silane gas, where the volumetric ratio of diborane gas to silane gas is 2% or more. Layer 1252 has been successfully implemented by sputtering $VO_x$ over barrier layer 1170 under deposition conditions that obtain required electrical and thermal characteristics and low compressive stress to prevent deformation and provide flatness in layer 1162.

Low noise thermistors with high thermal sensitivity have been successfully produced by sputtering a metallic vanadium target material in a mixed argon/oxygen plasma. Sputtering can be performed at room temperature and the resulting layer 1252 includes primarily and predominantly $V_2O_5$ together with other oxides of vanadium and some vanadium hydroxide. The term "surface oxide" is used herein to refer to a thin layer spontaneously formed on the surface of a semiconductor in an atmosphere containing oxygen; a surface oxide on a semiconductor typically plays a role as a passivation layer that eliminates dangling bonds and surface traps (thus reducing noise). A surface oxide on vanadium oxide could include any combination of one or more of the following: single or double bond vanadium oxides or vanadium hydroxide. In addition, vanadium hydrides ($VH_x$) could also be formed as a passivation layer. These materials are therefore referred to herein collectively as "vanadium surface oxides".

$V_2O_5$ acts as a semiconductor at room temperature, meaning that the sputtering chamber must be cleaned to remove any metallic impurities that would degrade its properties prior to sputtering. In addition, the vanadium target needs to be cleaned to remove $VO_x$ redeposits and contaminations that may have formed during previous sputtering operations. By taking these precautions, it has been possible to obtain a very clean, pure layer of $VO_x$ at a thickness of 300 nm, allowing thermal sensors with NETD not greater than 100 μK over a bandwidth range of 1-4.2 Hz, and possibly an order of magnitude less, i.e. not greater than 10 μK over the same bandwidth range, under appropriate calorimeter operating conditions.

Although DC sputtering of $VO_x$ has proved successful in producing low noise thermistors, it is foreseeable that other deposition techniques would also be successful if performed with appropriate parameters. For example, $VO_x$ could be deposited by thermal evaporation, electron beam evaporation, or by a sol-gel coating method.

After layer 1252 has been deposited, an annealing operation improves low noise characteristics. In particular, annealing in an appropriate gas such as $N_2$ at a suitable temperature for an appropriate period of time decreases resistivity of layer 1252 and reduces 1/f noise level of a resulting thermistor. Sheet resistance values on the order of 400 KΩ/square have been obtained for a 300 nm thick film of $VO_x$.

Some characteristics of $VO_x$ films have been observed by fabricating $VO_x$ on glass substrates. The microscopic structure of such $VO_x$ films has low compressive stresses, in the range −55 to −75 Mpa, and may be nanocrystalline or amorphous. Grain sizes of 10 nm and smaller have been observed, and small grain size may play a role in low noise behavior of $VO_x$ films.

More specifically, Hooge, F. N., "1/f noise is no surface effect", *Physics Letters*, Vol. 29A, No. 3, 1969, pp. 139-140, proposed a useful empirical model for reducing 1/f noise in semiconductors, expressed as follows:

$$V_n^2(V^2/Hz) = KF \frac{q \cdot \mu \cdot \rho \cdot V_B^2}{W \cdot L \cdot t} \cdot \frac{1}{f} \quad \text{(Eq. 2)}$$

where KF is an empirical factor called the Hooge factor; $V_n^2$ is the square of the voltage noise density; q is the electron charge; μ is carrier mobility; ρ is electrical resistivity; $V_B$ is voltage drop over the resistor; W, L, and t are the width, length, and thickness of the resistor, respectively; and f is the frequency.

Equation 2 indicates that a low noise thermistor can possibly be obtained by improving resistor design, by using lower resistive material, or by using material with a lower Hooge factor KF. The limited space available for cell 1200 limits the values of W and L, which therefore limits the improvement in noise that can be gained by designing the geometry of the resistor. Similarly, resistivity has lower limits that result from self-heating considerations and from the fact that TCR generally decreases with decreasing resistivity. For most semiconductors, TCR is proportional to activation energy, i.e. half of the band gap, and a smaller band gap generally corresponds to a smaller resistivity.

From these considerations, it follows that the Hooge factor KF is the factor most likely to reduce noise if optimized, and this approach has been followed for reducing excess 1/f noise in various semiconductors, including crystalline and amorphous semiconductors. In general, the Hooge factor is a material property and is highly dependent on processing conditions, surface passivation, and other detailed processing parameters. The operations performed in producing layer 1252 are therefore aimed to approximate an optimal Hooge factor KF for the material in layer 1252. It is believed that a near optimal value of KF for $VO_x$ can be obtained by room temperature sputtering from a vanadium target at DC sputtering power of 150-750 W with an argon/oxygen flow ratio in the range between 10:1 and 3:1 for a deposition time between 5-30 min under deposition pressure of 1.5-6 mTorr and by then annealing the sputtered $VO_x$, with the specific sputtering parameter from each range being chosen to obtain the optimal value with the sputtering apparatus or equipment being used. In particular, this technique has been used with a vanadium target under a mixed argon/oxygen ambient to obtain a film of room-temperature DC-sputter-deposited $VO_x$ that is primarily vanadium pentoxide ($V_2O_5$) and is 300 nm thick. Resulting characteristics of $VO_x$ produced in this manner are compared with other materials below.

Cross-section 1260 illustrates a subsequent stage in which layer 1252 has been patterned, such as by photolithographically producing an appropriate mask and then selectively removing layer 1252, leaving slab 1230 as well as other components such as slabs 1232, 1234, and 1236 (FIG. 14). Any suitable technique could be used, including wet etching, dry etching, or lift-off techniques. After patterning of layer 1252, conductive layer 1262 is deposited, such as by depositing a sandwich of Cr/Al/Cr or TiW/Al/Cr. If layer 1252 includes $VO_x$, TiW/Al/Cr may provide better ohmic contact with $VO_x$, improving noise performance. Lines, leads, and contact pads as shown in FIGS. 12 and 14, when implemented with materials such as these, can provide "low noise output circuitry", a term used herein to refer to circuitry that, if connected to one or more low noise thermal sensors such as low noise thermistors, provides an electrical output signal that includes no more than approximately twice the noise from the low noise thermal sensors. In other words, low noise output circuitry would contribute no more noise than would come from low noise thermal sensors to which it is connected.

Cross-section 1270 shows a subsequent stage at which layer 1262 has been patterned, such as by photolithographically producing a mask and performing selective removal as described above. After patterning of layer 1262, leads 1150 and 1152 extend across slab 1230 as well as around it, while merger portions 1272 and 1274 of drop merger 1240 are also produced. Other leads shown in FIG. 14 are also produced in this stage, as well as the contact pads, all of which include conductive material from layer 1262.

Then, top layer 1276 is deposited, such as by depositing protective layers 1172 and 1174 (FIG. 13). As described above, layer 1172 provides an upper barrier layer. Openings to expose contact pads can be etched through layer 1172, and a thin layer of TiAu or CrAu can then be sputtered and patterned with the same mask, such as by a lift-off process, to provide improved ohmic contact on the surfaces of the contact pads. On top of layer 1172, polymer layer 1174 is deposited, providing an additional barrier and a hydrophobic surface. Openings can then be etched through layer 1174 to expose the thin layer of TiAu or CrAu on the contact pads. The entire structure on the surface of polymer layer 1162 as shown in cross-section 1270 can be referred to as sensor structure 1278.

Cross-section 1280 shows the other side of polymer layer 1162 on which thermally conductive component 1160 has been formed. Cross-section 1280 also illustrates the relationship of component 1160 to sensor structure 1278, shown in profile on the other side of polymer layer 1162.

Component 1160 has been produced by depositing a 9 μm layer of copper, and then patterning it, such as by photolithographically forming a mask and performing selective removal as described above, producing thermally conductive component 1160. In one implementation of this technique, the starting substrate is a pre-manufactured structure that includes polymer layer 1162 on which a layer of copper has been electrodeposited, such as by depositing one or more thin seed layers such as a chromium seed layer and a copper seed layer and then electroplating copper onto the seed layers; in this implementation, the layer of copper can be selectively removed at any appropriate point in the process to produce component 1160. Techniques for producing such a starting substrate are described in U.S. Pat. No. 4,863,808, incorporated herein by reference.

Anti-coupling coating 1164 is then deposited over component 1160. The need for anti-coupling coating 1164 may be reduced or eliminated, however, by using a pre-manufactured starting substrate as described above. More specifically, it may be possible to selectively remove an electroplated copper layer and leave one or more seed layers intact, in which case the remaining seed layers may prevent capacitive coupling and the resulting noise. In general, applicable anti-coupling measures are described in greater detail in co-pending U.S. patent application Ser. No. 11/167,746, entitled "Thermal Sensing" and incorporated herein by reference in its entirety.

After deposition of coating 1164, the resulting structure can be cut off of the frame on which it was mounted during processing and can be attached to frame 1202 (FIG. 14). Frame 1202 acts as a stiffener to hold layer 1162 taut and flat. Further operations can be performed, such as laser trimming of slabs 1142 and 1144 to balance bridge 1102.

When connected in circuit 1100 (FIG. 11), cell 1200 can be operated as follows: Two drops of approximately 250 nl can be released on each of drop mergers 1240 and 1242. The drops on one merger can initiate a reaction such as a protein-ligand binding reaction, an enzymatic reaction, or an organelle activity, while the drops on the other merger can be non-reactive, providing a reference for differential measurement. After the drops reach thermal equilibrium, the drops on both mergers can be concurrently merged and mixed by applying appropriate voltage signals across contact pads 1222 and 1224, as described in the Torres et al. article, incorporated by reference above.

A thermal input signal resulting from merging and mixing of drops is conducted downward through sensor structure 1278 and part of layer 1162 to thermally conductive component 1160. Then, the thermal input signal is conducted laterally through component 1160 to the regions under slabs 1230 and 1232, where they are conducted upward to slabs 1230 and 1232 through part of layer 1162 and layer 1170. A change in temperature in the slabs on one side of cell 1200 changes their resistance, resulting in detection of current through measuring thermistors 1110. The current's magnitude indicates the temperature difference between measuring thermistors 1110 and reference thermistors 1112.

If cells 1230, 1232, 1234, and 1236 include vanadium oxide, the implementation of FIGS. 12-15 thus illustrates an example of a calorimeter in which a resistive thermometer element includes vanadium oxide. The calorimeter also includes circuitry through which electrical resistance of the thermometer element can be detected, exemplified by the leads and pads in FIG. 14. The calorimeter also includes a structure with a reaction region in which reactions that produce thermal change occur, exemplified by the region in which drops are merged. The structure conducts temperature from reactions in the reaction region to the thermometer element, illustratively through component 1160.

The implementation of FIGS. 12-15 with vanadium oxide also illustrates an example of a calorimeter in which a thermal sensor includes a thermistor that includes vanadium oxide. The thermal sensor has NETD not greater than approximately 100 μK over a bandwidth range of approximately 3 Hz or more under the calorimeter's operating conditions. The calorimeter also includes a structure with a thermal conducting path that provides a thermal input signal to the thermistor, exemplified by islands 1204 and 1206. The calorimeter also includes detecting circuitry connected to the thermal sensor, exemplified by leads 1150, 1152, 1154, and 1156; the detecting circuitry allows electrical detection of information about the thermal input signal.

The implementation of FIGS. 12-15 also illustrates an example of a calorimeter with a set of one or more low noise thermistors, exemplified by slabs 1230, 1232, 1234, and 1236. The calorimeter also includes a structure with one or more thermal conducting paths, each of which provides a respective thermal input signal to a respective subset of the thermistors, exemplified by islands 1204 and 1206. The calorimeter also includes low noise detection circuitry connected to the thermistors, exemplified by the lines, leads, and pads in FIG. 14; the detection circuitry allows electrical detection of information about the thermal input signals.

Figure 16:
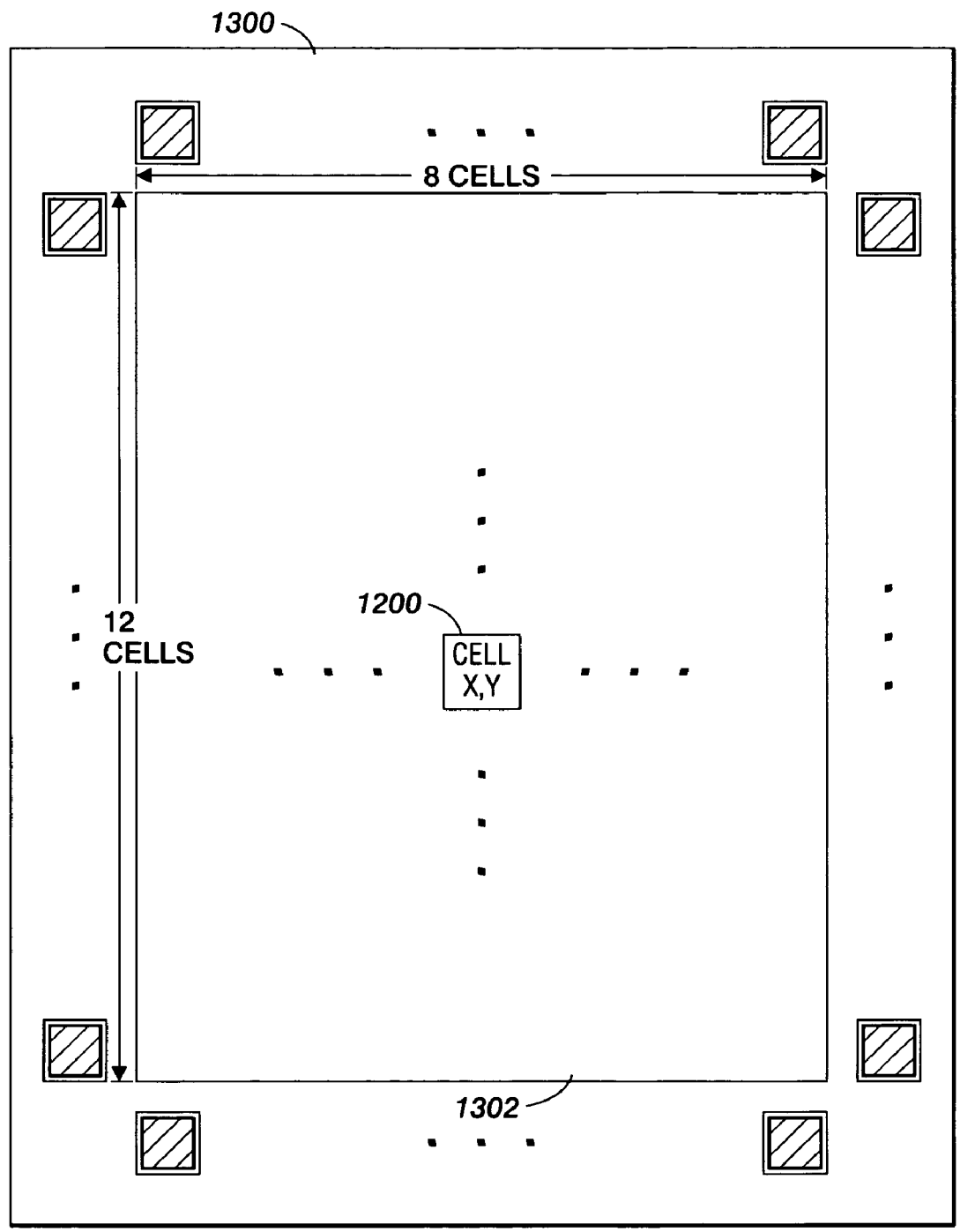
FIG. 16 is a schematic layout diagram of an integrated circuit that includes an array of thermal sensing cells like that shown in FIG. 14.

FIG. 16 shows how an array of cells similar to cell 1200 (FIG. 14) can be integrated on substrate 1300. As shown, array 1302 is 8 cells wide by 12 cells long. To interface with standard automated laboratory equipment, the cells are positioned on 9 mm centers and the automated laboratory equipment connects with the contact pads of each cell as described above. Array 1302 can be one of several arrays fabricated on a single substrate. Features of arrays and cells are also described in co-pending U.S. patent application Ser. No. 11/167,635, entitled "Thermal Sensing" and incorporated herein reference in its entirety.

If implemented with vanadium oxide thermistors, the array of FIG. 16 thus illustrates an example of an array with calorimeters, each including a set of resistive thermometer elements that include vanadium oxide. Each calorimeter also includes circuitry through which electrical resistance of the thermometer elements can be detected. Each calorimeter also includes a structure with a reaction region in which reactions that produce thermal change occur. The structure conducts temperature from reactions in the reaction region to at least one of the thermometer elements.

The implementations of FIGS. 12-16 include many features that are merely illustrative and could be modified within the scope of the invention. For example, features could be included as described in the Torres et al. article, incorporated by reference above.

More generally, the implementations of FIGS. 12-16 are advantageous because they permit high sensitivity and high throughput in a label free calorimetric detection system, such as in proteomic and drug development research. Sensitivities as fine as single-digit microdegree resolution or better can be achieved, and the noise level of thermistors as described can approach the Johnson noise level. At the same time, other material properties that affect resolution are preserved, such as high TCR, thus improving the overall signal-to-noise ratio of an instrument. As a result, the array of FIG. 16 can advantageously be implemented to measure thermal change from merged drops with single digit micromolar concentrations of molecules.

Figure 17:
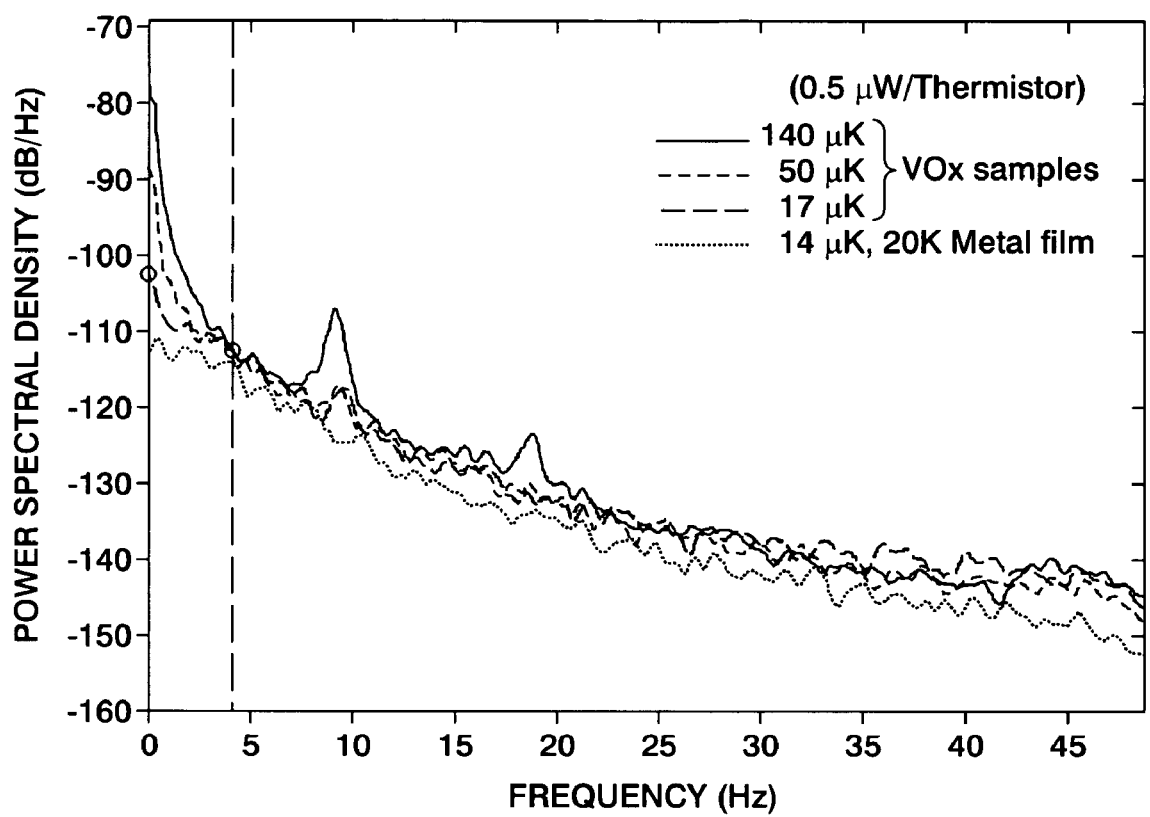
FIG. 17 shows graphs of estimated noise power spectral density as a function of frequency for three vanadium oxide samples and a reference metal film.

As noted above in relation to FIG. 15, low noise thermistors can be produced with $VO_x$. FIG. 17 illustrates graphically the 1/f noise from three samples of $VO_x$ and from a reference sample of 20K metal film, which should approach Johnson noise level. More specifically, the estimated noise power spectral density (PSD) of each sample, obtained as a Welch estimate (in dB/Hz), is plotted as a function of frequency (in Hz). In general, the reference sample has a lower PSD than the $VO_x$ samples at nearly all frequencies, but it can be seen from FIG. 17 that, for all the $VO_x$ samples, the noise is only slightly greater than that of the reference sample. For reference, the vertical dashed line in FIG. 17 represents 4.2 Hz, the upper limit of a typical measurement bandwidth for amplifier 1106 (FIG. 11) for bio-measurements, i.e. 0.1 Hz-4.2 Hz.

Figure 18:
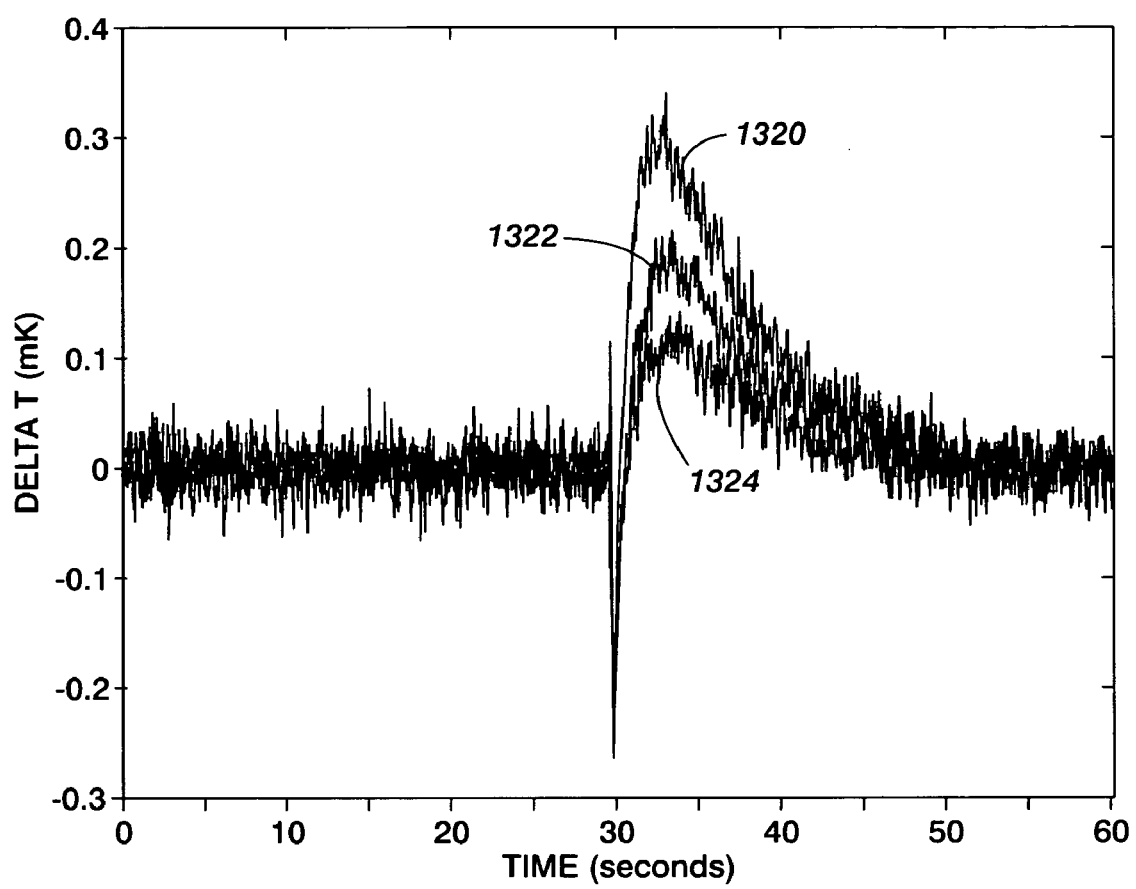
FIG. 18 is a graph superimposing three temperature measurements made with a vanadium oxide thermal sensor, each shown as a function of time.

FIG. 18 illustrates noise from a $VO_x$ thermal sensor in a different way. Three temperature measurements made with a $VO_x$ thermal sensor in a cell similar to the one in FIG. 14 are superimposed in a way that contrasts measured temperatures during reactions. The three measurements resulted in curves 1320, 1322, and 1324 immediately following merger of drops of the "DC-sign" protein present in HIV and an oligosaccharide called "Man9". In each case, the reaction caused a sharp temperature rise after merger and then the temperature decayed exponentially back to steady state, and the curves provide information about this thermal signal. At the measured values, the maximum noise amplitude is approximately 0.05 mK for each of curves 1320, 1322, and 1324. In contrast, the noise occurring with previous thermal sensors in which thermistors include heavily n-doped amorphous silicon was greater than 0.1 mK, in which case curve 1324 in FIG. 18 would be nearly undistinguishable from noise, and curves 1320 and 1322 would be only slightly greater than the noise.

FIG. 18 thus illustrates electrical output signals that are time-varying signals with noise peaks that have amplitudes not exceeding a maximum noise amplitude, illustratively approximately 50 μK. The output signals include signal peaks with amplitudes exceeding the maximum noise amplitude, and these peaks provide information about the thermal input signal.

FIG. 18 also illustrates an example in which thermal input signals have peaks with amplitude less than approximately 350 μK, and the electrical output signal includes information about at least one of those peaks. Indeed, the electrical output signal includes information about a peak in curve 1324 that has an amplitude of approximately 100 μK.

The techniques described above, are not, however, limited to application in which electrical output signals include information about peaks with amplitude less than approximately 350 μK. Information about peaks with larger amplitudes can also be obtained, as would typically occur, for example, in calorimetry application with lower sensitivity and higher throughput.

FIG. 18 illustrates just one way in which an output signal can include information about thermal input signals. Specifically, the output signals in FIG. 18 have amplitudes that indicate amplitudes of thermal input signals, but other information about thermal input signals could be obtained and amplitude or other information could be included in or indicated by an output signal in various other ways.

FIGS. 19 and 20 show how thermal sensitivity of $VO_x$ samples has been verified by measuring temperature dependence of film resistance. Typical expected behavior for a semiconductor with mobile carrier density controlled by thermal excitation is:

$$R(T) = R_0 \exp\left(\frac{\Delta E}{kT}\right) \quad \text{(Eq. 3)}$$

with E the activation energy (half the band gap). The TCR is then:

$$TCR = \frac{dR}{RdT} = \frac{\Delta E}{kT^2} \quad \text{(Eq. 4)}$$

FIGS. 19 and 20 show typical measurement data of a $VO_x$ sample, and correspond well with the above thermal excitation model. FIG. 19 shows resistivity as a function of inverse temperature, and does not include a semiconductor-metal transition as would be expected for pure vanadium dioxide ($VO_2$) around 70° C.; this tends to confirm that the material produced as described above consists mainly of other oxides of vanadium, such as primarily vanadium pentoxide ($V_2O_5$). FIG. 20 shows $\ln(R/R_0)$ as a function of temperature for a small region around room temperature, the typical operating condition in nanocalorimetry experiments. The solid line in FIG. 20 is a linear approximation and can be expressed as y=−0.0304x+0.6863. The magnitude of the slope, 3.04%/K, is therefore a room temperature TCR value; typical measured values of TCR for $VO_x$ films lie between 3 and 4%/K.

FIG. 21 compares measured noise data over the frequency interval 1-4.2 Hz for thermal sensors with $VO_x$ thermistors produced by magnetron sputtering at room temperature with noise data for thermal sensors with two types of amorphous silicon thermistors. One type of thermistor included heavily n-doped amorphous silicon deposited by PECVD at 230° C. and 274° C., the material previously used for similar thermistors; the other type of thermistor included heavily p-doped amorphous silicon deposited by PECVD at 330° C. As shown, NETDs below 10 μK were obtained for thermal sensors with $VO_x$ thermistors, but thermal sensors with n-doped amorphous silicon thermistors had NETDs around 70 μK. Both samples of thermal sensors with p-doped amorphous silicon thermistors had NETDs around 8-11 μK, suggesting that p-doped amorphous silicon could also be used in low noise thermistors; on the other hand, its high PECVD deposition temperature would complicate fabrication on a polyimide substrate, and a process with sputtering of $VO_x$ may be more economical because it is easier and less expensive to transfer to a manufacturing environment than a process with PECVD deposition of amorphous silicon. It is foreseeable that other materials may be produced with high TCRs, leading to thermal sensors with low NETDs; such materials could include, for example, yttrium barium copper oxide (YBCO), titanium oxide ($TiO_x$), and zinc oxide ($ZnO_x$).

NETD values as in FIG. 21 are a function of applied bias and power. FIGS. 22-25 illustrate dependence of noise on applied bias voltage and power for samples of thermal sensors with $VO_x$ thermistors. In each case, noise is measured over the frequency interval 1-14.2 Hz, a bandwidth range that is used here as a metric for each material but that does not necessarily correspond to the best temperature resolution that can be expected in a measurement—typically signals on a timescale of a few seconds are of interest and therefore will include 1/f noise contributions at frequencies below 1 Hz.

In FIG. 22, the data points and fitted curve 1340 show noise voltage as a function of bias voltage $V_B$ as in bridge 1102 in FIG. 11. In contrast, line 1342 shows the calculated Johnson noise for a 38 KΩ resistor, which is independent of bias voltage. The data points in FIG. 23 similarly show noise voltage as a function of dissipated power on one side of the bridge, i.e. the power dissipated in a pair of thermistors. In this experiment, each thermistor in the bridge included a $VO_x$ sample with resistance of 38 KΩ. At low bias voltages, Johnson and system noise is dominant, totaling around 50 nV, but as bias voltage increases, the effect of 1/f noise emerges, with 1/f noise increasing approximately linearly with bias current flowing through the resistor.

The data points in FIG. 24 show NETD of a sample thermal sensor with $VO_x$ thermistors as a function of bias voltage, while the data points in FIG. 25 show NETD as a function of dissipated power. For these measurements, the effect of 1/f noise corresponds to saturation of the decrease in NETD versus bias voltage (illustratively around 2 V in FIG. 24); in absence of 1/f noise, this relation would be hyperbolic in the bias voltage in accordance with Eq. 1, above. In practice, the 1/f noise limits the gain in sensitivity that can be obtained by increasing the bias voltage across bridge 1102. For $VO_x$, the limit occurs well below 5 μK, as shown in FIG. 24.

FIGS. 24 and 25 both illustrate examples in which NETD of a thermal sensor with a thermistor that includes $VO_x$ is not greater than approximately 35 μK, as illustrated by the leftmost and highest point on each curve, and also illustrate examples in which NETD is not greater than approximately 10 μK, as illustrated by the fourth and subsequent points on each curve.

The maximum power and bias voltage that can be used in a nanocalorimetric measurement are limited by a measurement system's finite common-mode rejection ratio and by asymmetries between reference and measurement sites which could, for example, result in different thermal resistances to the environment. A practical limit currently used is 1-5 μW, but, as shown in FIG. 25, this range does not allow operation in the lowest noise regime, which occurs at higher power levels. Improved matching of bridge 1102 and matching of dissipated power on reference and measurement sites would allow operation at higher power levels.

The techniques described above are useful for calorimetry measurements, such as in biophysical and biochemical studies to determine energy changes as indications of biochemical reactions. Calorimetry measurements are useful in a broad variety of application, including, for example, pharmaceuticals (drug discovery, decomposition reactions, crystallization measurements), biology (cell metabolism, drug interactions, fermentation, photosynthesis), catalysts (biological, organic, or inorganic), electrochemical reactions (such as in batteries or fuel cells), polymer synthesis and characterization, and so forth. In general, calorimetry measurements can be useful in the discovery and development of new chemicals and materials of many types, as well as in the monitoring of chemical processes.

In addition to calorimetry application, techniques described above may be used in various other thermal sensing application.

In the implementations described above, bridges illustratively have one terminal receiving an AC drive voltage and another connected to ground, but the same terminals could receive any other appropriate combination of voltages. For example, the terminal connected to ground could instead be connected to some other voltage different than the AC drive voltage, or the bridge could be driven by a balance transformer in which case the terminals are driven with opposite polarities relative to ground. Any of these variations would be within the foreseeable scope of variations.

Some of the above exemplary implementations involve specific materials, such as amorphous silicon or vanadium oxide in thermistors; any of various polymers in a supporting layer; copper, aluminum, chromium, TiW, or a combination of them in conductive components; silicon oxynitride in barrier layers; and so forth, but the invention could be implemented with a wide variety of materials and with layered structures with various combinations of sublayers. In particular, other substrate materials such as silicon or other types of support structures could be used besides those specified above, and a wide variety of materials could be used in device layers, insulating layers, leads, lines, electrodes, and other components; for example, a top coating of sputter deposited $SiO_x$ or PECVD SiO or SiN could be provided. In addition, components could have various shapes, dimensions, or other numerical or qualitative characteristics other than those illustrated and described above.

Some of the above exemplary implementations involve two-dimensional arrays of thermal sensor cells with specified circuitry including circuitry connecting sensors as in a Wheatstone bridge and with a drop merging component, but the invention could be implemented with a single cell or with a one-dimensional array and with any suitable thermal sensor circuitry, with or without a Wheatstone bridge and with or without a drop merger. Furthermore, the above exemplary implementations generally involve cells with particular circuitry for other power and signal functions, but various other arrangements could be used.

The above exemplary implementations generally involve production and use of thermal sensors, devices, cells, and arrays following particular operations, but different operations could be performed, the order of the operations could be modified, and additional operations could be added within the scope of the invention. For example, as noted above, vanadium oxide could be deposited in any of several different ways. Also, the positioning of components on the sides of a polymer layer or other support structure could be modified within the scope of the invention. During use, electrical signals could be provided to components in any appropriate sequence.

While the invention has been described in conjunction with specific exemplary implementations, it is evident to those skilled in the art that many other alternatives, modifications, and variations will be apparent in light of the foregoing description. Accordingly, the invention is intended to embrace all other such alternatives, modifications, and variations that fall within the spirit and scope of the appended claims.

What is claimed is:

1. A calorimeter comprising:
a resistive thermometer element that includes vanadium oxide;
circuitry through which electrical resistance of the thermometer element can be detected; and
a structure with a reaction region in which reactions that produce thermal change occur, the structure conducting temperature from reactions in the reaction region to the thermometer element.

2. A calorimeter comprising:
a resistive thermometer element that includes vanadium oxide;
circuitry through which electrical resistance of the thermometer element can be detected; and
a structure with a reaction region in which reactions that produce thermal change occur, the structure conducting temperature from reactions in the reaction region to the thermometer element; the reaction region and the thermometer element being spaced apart; the structure further including a component with high thermal conductivity that is in thermal contact with the reaction region and with the thermometer element.

3. The calorimeter of claim 2 in which the thermometer element is made from thin film materials.

4. The calorimeter of claim 2 in which the vanadium oxide in the thermometer element has a high temperature coefficient of resistivity.

5. The calorimeter of claim 2 in which the reaction region is on a surface, the calorimeter further comprising a drop merging component that causes drops on the surface to merge in the reaction region.

6. A calorimeter comprising:
a thermal sensor that includes a thermistor, the thermistor including vanadium oxide; the thermal sensor having noise equivalent temperature difference (NETD) not greater than approximately 100 μK over a bandwidth range of approximately 3 Hz or more under the calorimeter's operating conditions;
a structure with a thermal conducting path that provides a thermal input signal to the thermistor; the thermistor being on the structure; the structure including:
a polymer layer; and
a barrier layer between the thermistor and the polymer layer; and
detecting circuitry connected to the thermal sensor, the detecting circuitry allowing electrical detection of information about the thermal input signal provided by the thermal conducting path.

7. The calorimeter of claim 6 in which the thermal sensor's NETD is not greater than approximately 35 μK over a bandwidth range of approximately 3 Hz or more under the calorimeter's operating conditions.

8. The calorimeter of claim 7 in which the thermal sensor's NETD is not greater than approximately 10 μK over a bandwidth range of approximately 3 Hz or more under the calorimeter's operating conditions.

9. A calorimeter comprising:
a set of one or more low noise thermistors; each low noise thermistor having noise equivalent temperature difference not greater than approximately 50 μK over a thermal sensing bandwidth range of approximately 3 Hz or more under the calorimeter's operating conditions;
a structure with one or more thermal conducting paths, each thermal conducting path providing a respective thermal input signal to a respective subset of the set of thermistors; at least one thermistor in the subset including vanadium oxide; each thermistor in the subset being on the structure; the structure including;
a polymer layer: and
a barrier layer between the thermistors in the subset and the polymer layer; and
low noise detection circuitry connected to the set of thermistors, the detection circuitry allowing electrical detection of information about the thermal input signals provided by the thermal conducting paths.

10. The calorimeter of claim 9, further comprising output circuitry connected to the detection circuitry, the output circuitry electrically detecting information about the thermal input signals and, in response, providing an electrical output signal; the electrical output signal being a time-varying signal that includes noise peaks with amplitudes not exceeding a maximum noise amplitude; the electrical output signal also including signal peaks indicating information about the thermal input signal, each signal peak's amplitude exceeding the maximum noise amplitude.

11. An array comprising: not less than one calorimeter; each calorimeter comprising:
a set of resistive thermometer elements, each including vanadium oxide;
circuitry through which electrical resistance of the thermometer elements can be detected; and
a structure with a reaction region in which reactions that produce thermal change occur, the structure conducting temperature from reactions in the reaction region to at least one of the thermometer elements; the reaction region and the at least one thermometer element being spaced apart; the structure further including a component with high thermal conductivity that is in thermal contact with the reaction region and with the at least one thermometer element.exceeding the maximum noise amplitude.

12. A calorimeter comprising:
a support structure that includes a polymer layer and a barrier layer;
a thermal sensor that includes one or more thermistors that are on the support structure with the barrier layer between the polymer layer and the thermistors, each of the thermistors including vanadium oxide; and
detecting circuitry electrically connected to the thermal sensor;

the support structure including at least one thermal conducting path that provides thermal input signals to at least one of the thermistors that are on the support structure, the detecting circuitry allowing electrical detection of information about the thermal input signals provided by the thermal conducting path.

13. The calorimeter of claim 12 in which the barrier layer includes silicon oxynitride.

14. The calorimeter of claim 12, further comprising one or more cells, each cell including a respective instance of the thermal sensor and the detecting circuitry; each thermistor including primarily $V_2O_5$.

15. The calorimeter of claim 12, further comprising one or more cells, each cell including a respective instance of the thermal sensor and the detecting circuitry; the barrier layer including silicon oxynitride.

16. The calorimeter of claim 12 in which the thermistor includes primarily $V_2O_5$.

17. The calorimeter of claim 16 in which the thermistor further includes one or more vanadium surface oxides other than $V_2O_5$.

18. A method of producing a calorimeter, comprising:
producing a resistive thermometer element, circuitry through which electrical resistance of the thermometer element can be detected, and a structure with a reaction region in which reactions that produce thermal change occur;
the structure conducting temperature from reactions in the reaction region to the thermometer element; the reaction region and the thermometer element being spaced apart; the structure further including a component with high thermal conductivity that is in thermal contact with the reaction region and with the thermometer element;
the act of producing the resistive thermometer element, the circuitry, and the structure comprising:
producing the resistive thermometer element to include vanadium oxide.

19. The method of claim 18 in which the resistive thermometer element includes primarily $V_2O_5$.

20. The method of claim 18 in which the act of producing the resistive thermometer element includes:
sputtering a metallic vanadium target material at room temperature in a plasma that includes oxygen.

21. A calorimeter comprising:
a set of one or more low noise thermistors; each low noise thermistor having noise equivalent temperature difference not greater than approximately 50 μK over a thermal sensing bandwidth range of approximately 3 Hz or more under the calorimeter's operating conditions;
a structure with one or more thermal conducting paths, each thermal conducting path providing a respective thermal input signal to a respective subset of the set of thermistors; at least one thermistor in the subset including vanadium oxide: each thermistor in the subset being on the structure: the structure including:
a polymer layer: and
a barrier layer between the thermistors in the subset and the polymer layer: and
low noise output circuitry connected to the set of thermistors, the output circuitry electrically detecting information about the thermal input signals and, in response, providing an electrical output signal that includes detected information about the thermal input signals provided by the thermal conducting paths.
in which at least one of:
the thermal input signal of one of the thermal conductive paths has peaks with amplitude less than approximately 350 μK; and
the structure includes two or more of the thermal conductive paths and at least two of the respective thermal input signals have a difference between them, the electrical output signal including detected information about the difference.

22. The calorimeter of claim 21 in which the set of thermistors includes first and second subsets, each thermistor in the first subset receiving a first thermal input signal from a first one of the thermal conducting paths and each thermistor in the second subset receiving a second thermal input signal from a second one of the thermal conducting paths; the electrical output signal including detected information about the difference between the first and second thermal input signals.

23. The calorimeter of claim 21 in which the thermal input signal of one of the thermal conducting paths includes peaks with amplitude less than approximately 350 μK; the electrical output signal including signal peaks indicating detected information about at least one of the peaks with amplitude less than approximately 350 μK.

24. The calorimeter of claim 21 in which the peaks in the thermal input signal of the one of the thermal conducting paths include a subset of peaks with amplitude of approximately 100 μK; the electrical output signal including signal peaks indicating detected information about at least one of the peaks in the subset.

* * * * *